US006699477B2

(12) United States Patent
Khanna et al.

(10) Patent No.: US 6,699,477 B2
(45) Date of Patent: Mar. 2, 2004

(54) EBV CTL EPITOPES

(75) Inventors: Rajiv Khanna, Herston (AU); Beverley Mavis Kerr, Gumdale (AU); Ihor Stephan Misko, St. Lucia (AU); Denis James Moss, Arana Hills (AU); Scott Renton Burrows, Bald Hills (AU)

(73) Assignees: The Council of the Queensland Institute of Medical Research, Queensland (AU); CSL Limited, Victoria (AU); Biotech Australia PTY Limited, New South Wells (AU); The Walter & Eliza Hall Institute of Medical Research, Victoria (AU); The University of Melbourne, Parkville (AU); Commonwealth Scientific and Industrial Research Organisation, Act (AU)

( * ) Notice: Subject to any disclaimer, the term of this patent is extended or adjusted under 35 U.S.C. 154(b) by 0 days.

(21) Appl. No.: 09/920,174

(22) Filed: Aug. 1, 2001

(65) Prior Publication Data

US 2002/0150590 A1 Oct. 17, 2002

Related U.S. Application Data

(63) Continuation of application No. 09/194,450, filed as application No. PCT/AU97/00328 on May 23, 1997, now abandoned.

(30) Foreign Application Priority Data

May 24, 1996 (AU) ............................................. PO 0073

(51) Int. Cl.[7] ................................................ A61K 39/12
(52) U.S. Cl. ................................ 424/204.1; 424/186.1; 424/230.1; 530/300; 536/23.72
(58) Field of Search .......................... 424/230.1, 204.1, 424/143.1, 186.1, 278.1; 435/69.1, 343, 343.2; 536/23.72; 530/300

(56) References Cited

FOREIGN PATENT DOCUMENTS

WO     WO 95/24925     9/1995

OTHER PUBLICATIONS

Kerdiles et al, Journal of Virology, Apr. 1990, vol. 64, No. 4, pp. 1812–1816.*
Adldinger et al., "A putative transforming gene of Jijoye virus differs from that of Epstein–Barr virus prototypes," *Virology*, 141:221–234, 1985.
Andrew et al., "The roles of influenza virus haemagglutinin and nucleoprotein in protection: analysis using vaccinia virus recombinants," *Scand. J. Immunol.*, 25:21–28, 1987.
Apolloni and Sculley, "Detection of A–type and B–type Epstein–Barr virus in throat washings and lymphocytes," *Virology*, 202:978–981, 1994.
Bogedain et al., "Specific cytotoxic T lymphocytes recognize the immediate–early transactivator Zta of Epstein–Barr virus," *J. Virol.*, 69:4872–4879, 1995.
Brooks et al., "Different HLA–B27 subtypes present the same immunodominant Epstein–Barr virus peptide," *J. Exp. Med.*, 178:879–887, 1993.
Buisson et al., "Changes in the dominant Epstein–Barr virus type during human immunodeficiency virus infection," *J. Gen. Virol.*, 75:431–437, 1994.
Burrows et al., "An Epstein–barr virus–specific cytotoxic T–cell epitope present on A– and B–type transformants," *Journal of Virology*, 64(8):3974–3976, 1990.
Burrows et al., "Bystander apoptosis induced by CD8+ cytotoxic T cell (CTL) clones: implications for CTL lytic mechanisms," *Int. Immunol.*, 5:1049–1058, 1993.
Burrows et al., "The specificity of recognition of a cytotoxic T lymphocyte epitope," *Eur. J. Immunol.*, 22:191–195, 1992.
Burrows et al., "Five new cytotoxic T cell epitopes identified within Epstein–Barr virus nuclear antigen 3," *J. Gen. Virol.*, 75:2489–2493, 1994.
Crawford et al., "Epstein–Barr virus nuclear antigen positive lymphoma after cyclosporin A treatment in patient with renal allograft," *Lancet*, 1:1355–1356, 1980.
Dambaugh et al., U2 region of Epstein–Barr virus DNA may encode Epstein–Barr nuclear antigen 2, *Proc. Natl. Acad. Sci. USA*, 81:7632–7636, 1984.
Doherty et al., "Evasion of host immune responses by tumours and viruses," *Ciba. Found. Symp.*, 187:245–260, 1994.
Fazekas de St. Groth, "The evaluation of limiting dilution assays," *J. Immunol. Methods*, 49:R11–23, 1982.
Gavioli et al., "Multiple HLA A11–restricted cytotoxic T–lymphocyte epitopes of different immunogenicities in the Epstein–Barr virus–encoded nuclear antigen 4," *J. Virol.*, 67:1572–1578, 1993.
Gratama et al., "Detection of multiple 'Ebnotypes' in individual Epstein–Barr carriers following lymphocyte transformation by virus derived from peripheral blood and oropharynx," *J. Gen. Virol.*, 75:85–94, 1994.
Gregory et al., "Different Epstein–Barr virus–B cell interactions in phenotypically distinct clones of a Burkitt's lymphoma cell line," *J. Gen. Virol.*, 71:1481–1495, 1990.
Henle et al., "Rheumatoid factor as a cause of positive reactions in tests for Epstein–Barr virus–specific IgM Antibodies," *Clin. Exp. Immunol.*, 36:415–422, 1979.

(List continued on next page.)

Primary Examiner—Ali R. Salimi
(74) Attorney, Agent, or Firm—Fulbright & Jaworski

(57) ABSTRACT

The present invention provides an isolated cytotoxic Epstein-Barr virus T-cell epitope having the amino acid sequence TYSAGIVQI (SEQ ID NO: 34) which can be formulated as a water-in-oil formulation, and vaccine compositions comprising said epitope, optionally with additional epitopes.

10 Claims, 9 Drawing Sheets

OTHER PUBLICATIONS

Henle and Henle, "Seroepidemiology of the virus," In: The Epstein–Barr Virus, Epstein and Achong (eds.), 61–78, 1979.

Hill et al., "Characterization of two Epstein–Barr virus epitopes restricted by HLA–B7," Eur. J. Immunol., 25:18–24, 1995.

Hill et al., "Class I major histocompatibility complex–restricted cytotoxic T lymphocytes specific for Epstein–Barr virus (EBV) nuclear antigens fail to lyse the EBV–transformed B lymphoblastoid cell lines against which they were raised," J. Exp. Med., 181:2221–2228, 1995.

Fu et al., "Variable expression of latent membrane protein in nasopharyngeal carcinoma can be related to methylation status of the Epstein–Barr virus BNLF–1 5'–flanking region," J. Virol., 65:1558–1567, 1991.

Kerr et al., "Identification of type B–specific and cross–reactive cytotoxic T–lymphocyte responses to Epstein–Barr virus," Journal of Virology, 70(12):8858–8864, 1996.

Khanna et al., "Localization of Epstein–Barr virus cytotoxic T–cell epitopes using recombinant vaccinia: implications for vaccine development," J. Exp. Med., 176:169–176, 1992.

Khanna et al., Immune regulation in Epstein–Barr virus–associated diseases,: Microbiol. Rev., 59:387–405, 1995.

Khanna et al., "Expression of Epstein–Barr virus nuclear antigens in anti–IgM–stimulated B cells following recombinant vaccinia infection and their recognition by human cytotoxic T–cells," Immunology, 74:504–510, 1991.

Khanna et al., "Isolation of cytotoxic T lymphocytes from healthy seropositive individuals specific for peptide epitopes from Epstein–Barr virus nuclear antigen 1: implications for viral persistence and tumor sruveillance," Virology, 214:633–637, 1995).

Kyaw et al., "Expression of B–type Epstein–Barr virus in HIV–infected patients and cardiac transplant recipients," AIDS Res. Hum. Retroviruses, 8:1869–1874, 1992.

Landau et al., "Presence of infective Epstein–Barr virus in the urine of patients with infectious mononucleosis," J. Med. Virol., 44:229–233, 1994.

Laroche et al., "Measurement by the polymerase chain reaction of the Epstein–Barr virus load in infectious monoucleosis and AIDS–related non–Hodgkins's lymphomas," J. Med. Virol., 46:66–74, 1995.

Lear et al., "The Epstein–Barr virus (EBV) nuclear antigen 1 BamHI F promoter is activated on entry of EBV–transformed B cells into the lytic cycle," J. Virol, 66:7461–7468, 1992.

Lee et al., "HLA A2.1 restricted cytotoxic T–cells recognizing a range of Epstein–Barr virus isolates through a defined epitope in latent membrane protein LMP2," J. Virol., 67:7428–7435, 1993.

Lewin et al., "Characterization of EBV–carrying B–cell populations in healthy seropositive individuals with regard to density, release of transforming virus and spontaneous outgrowth," Int. J. Cancer, 39:472–476, 1987.

Lung et al., "Epstein–Barr virus genotypes associated with nasopharyngeal carcinoma in southern China," Virology, 177:44–53, 1990.

Miller et al., An integral membrane protein (1mp2) blocks reactivation of Epstein–Barr virus from latency following surface immunoglobulin crosslinking, Proc. Natl. Acad. Sci. USA, 91:772–776, 1994.

Miller and Hutt–Fletcher, "A monoclonal antibody to glycoprotein gp85 inhibits fusion but not attachment of Epstein–Barr virus," J. Virol., 62:2366–2372, 1988.

Misko et al., "Factors influencing the human cytotoxic T–cell response to autologous lymphoblastoid cell lines in vitro," Clin. Immunol. Immunopathol., 32:285–297, 1984.

Miyashita et al., "A novel form of Epstein–Barr virus latency in normal B cells in vivo," Cell, 80:593–601, 1995.

Morgan et al., "A recombinant adenovirus expressing an Epstein–Barr virus (EBV) target antigen can selectively reactivate rare components of EBV cytotoxic T–lymphocyte memory in vitro," J. Virol., 70:2394–2402, 1996.

Moss et al., "Cytotoxic T–cell clones discriminate between A– and B–type Epstein–Barr virus transformants," Nature, 331:719–721, 1988.

Moss et al., "Long–term T–cell–mediated immunity to Epstein–Barr virus in man. Complete regression of virus–induced transformation in cultures of seropositive donor leukocytes," Int. J. Cancer, 22:662–668, 1978.

Murray et al., "Identification of target antigens for the human cytotoxic T–cell response to Epstein–Barr virus (EBV): implications for the immune control of EBV–positive malignancies," J. Exp. Med., 176:157–168, 1992.

Murray et al., "Human cytotoxic T–cell responses against Epstein–Barr virus nuclear antigens demonstrated by using recombinant vaccinia viruses," Proc. Natl. Acad. Sci. USA, 87:2906–2910, 1990.

Nilsson et al., "The establishment of lymphoblastoid lines from adult and fetal human lymphoid tissue and its dependence on EBV," Int. J. Cancer, 8:443–450, 1991.

Okano et al., "Severe chronic active Epstein–Barr virus infection syndrome," Clin. Microbiol. Rev., 4:129–135, 1991.

Polack et al., "A complete set of overlapping cosmid clones of M–ABA virus derived from nasopharyngeal carcinoma and its similarity to other Epstein–Barr virus isolates," Gene, 27:279–288, 1984.

Pope et al., "Burkitt lymphoma in New Guinea: establishment of a line of lymphoblasts in vitro and description of their fine structure," J. Natl. Cancer Inst., 39:933–945, 1967.

Pope et al., "Transformation of foetal human leucocytes in vitro by filtrates of a human leukaemic cell line containing herpes–like virus," Int. J. Cancer, 3:857–865, 1968.

Rammensee et al., "MHC ligands and peptide motifs: first listing," Immunogenetics, 41:178–228, 1995.

Ressing et al., "Human CTL epitopes encoded by human papillomavirus type 16 E6 and E7 identified through in vivo and in vitro immunogenicity studies of HLA–A 0201–binding peptides," J. Immunol., 154:5934–5943, 1995.

Rickinson et al., "T–cell mediated regression of spontaneous and of Epstein–Barr virus–induced B–cell transformation in vitro: studies with cyclosporin A," Cell. Immunol., 87:646–658, 1984.

Rickinson et al., "Influence of the Epstein–Barr virus nuclear antigen EBNA 2 on the growth phenotype of virus–transformed B cells," J. Virol., 61:1310–1317, 1987.

Rooney et al., "Paired Epstein–Barr virus–carrying lymphoma and lymphoblastoid cell lines from Burkitt's lymphoma patients: comparative sensitivity to non–specific and to allo–specific cytotoxic responses in vitro," Int. J. Cancer, 34:339–348, 1984.

Rooney et al., "Epstein–Barr virus–positive Burkitt's lymphoma cells not recognized by virus–specific T–cell surveillance," *Nature,* 317:629–631, 1985.

Rosenberg et al., "Biological activity of recombinant human interleukin–2 produced in *E. coli,*" *Science,* 223:1412–1414, 1984.

Sample and Kieff, "Transcription of the Epstein–Barr virus genome during latency in growth–transformed lymphocytes," *J. Virol.,* 64:1667–1674, 1990.

Schmidt et al., "Nonresponsiveness to an immunodominant Epstein–Barr virus–encoded cytotoxic T–lymphocyte epitope in nuclear antigen 3A: implications for vaccine strategies," *Proc. Natl. Acad. Sci. USA,* 88:9478–9482, 1991.

Sculley et al., "Coinfection with A– and B–type Epstein–Barr virus in human immunodeficiency virus–positive subjects," *J. Infect. Dis.,* 162:643–648, 1990.

Sculley et al., "Expression of Epstein–Barr virus nuclear antigens 3, 4 and 6 are altered in cell lines containing B–type virus," *Virology,* 171:401–408, 1989.

Selin et al., "Cross–reactivities in memory cytotoxic T lymphocyte recognition of heterologous viruses," *J. Exp. Med.,* 179:1933–1943, 1994.

Sixbey et al., "Detection of a second widespread strain of Epstein–Barr virus," *Lancet,* 2:761–765, 1989.

Silins et al., "Isolation of Epstein–Barr virus genomes using pulse–field gel electrophoresis," *Nucleic Acids Res.,* 20:2901, 1992.

Sumaya and Ench, "Epstein–Barr virus infectious mononucleosis in children. Clinical and general laboratory findings," *Pediatrics,* 75:1003–1010, 1985.

Sumaya and Ench, "Epstein–Barr virus infectious mononucleosis in children. Heterophil antibody and viral–specific responses," *Pediatrics,* 75(6):1011–1019, 1985.

Tomkinson et al., "Activated lymphocytes during acute Epstein–Barr virus infection," *J. Immunol.,* 139:3802–3807, 1987.

Tussey et al., "Different MHC class I alleles compete for presentation of overlapping viral epitopes," *Immunity,* 3:65–77, 1995.

Wagner et al., "Detection and quantification of latently infected B lympocytes in Epstein–Barr virus–seropositive, healthy individuals by polymerase chain reaction," *J. Clin. Microbiol.,* 30:2826–2829, 1992.

* cited by examiner

SEQUENCE LISTING

```
<160> NUMBER OF SEQ ID NOS: 50

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1

Thr Ser Leu Tyr Asn Leu Arg Arg Gly Thr Ala Leu Ala
  1               5                  10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 2

Asp Thr Pro Leu Ile Pro Leu Thr Ile Phe
  1               5                  10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 3

Thr Val Phe Tyr Asn Ile Pro Pro Met Pro Leu
  1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 4

Val Glu Ile Thr Pro Tyr Lys Pro Thr Trp
  1               5                  10

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 5
```

Val Ser Phe Ile Glu Phe Val Gly Trp
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Phe Arg Lys Ala Gln Ile Gln Gly Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Phe Leu Arg Gly Arg Ala Tyr Gly Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Gln Ala Lys Trp Arg Leu Gln Thr Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Ser Val Arg Asp Arg Leu Ala Arg Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Tyr Pro Leu His Glu Gln His Gly Met
1               5

<210> SEQ ID NO 11
<211> LENGTH: 9
<212> TYPE: PRT
<213> ORGANISM: Artificial Sequence
<220> FEATURE:

```
<223> OTHER INFORMATION: Description of Artificial Sequence:  Synthetic
      Peptide

<400> SEQUENCE: 11

His Leu Ala Ala Gln Gly Met Ala Tyr
 1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 12

Arg Pro Pro Ile Phe Ile Arg Arg Leu
 1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 13

Arg Leu Arg Ala Glu Ala Gly Val Lys
 1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 14

Ile Val Thr Asp Phe Ser Val Ile Lys
 1               5

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 15

Ala Val Phe Asp Arg Lys Ser Asp Ala Lys
 1               5                  10

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 16

Asn Pro Thr Gln Ala Pro Val Ile Gln Leu Val His Ala Val Tyr
 1               5                  10                  15
```

```
<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 17

Leu Pro Gly Pro Gln Val Thr Ala Val Leu Leu His Glu Glu Ser
 1               5                  10                  15

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

Asp Glu Pro Ala Ser Thr Glu Pro Val His Asp Gln Leu Leu
 1               5                  10

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

Arg Tyr Ser Ile Phe Phe Asp Tyr
 1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 20

Ala Val Leu Leu His Glu Glu Ser Met
 1               5

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 21

Arg Arg Ala Arg Ser Leu Ser Ala Glu Arg Tyr
 1               5                  10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 22
```

```
Glu Glu Asn Leu Leu Asp Phe Val Arg Phe
  1               5                  10
```

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 23

```
Lys Glu His Val Ile Gln Asn Ala Phe
  1               5
```

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 24

```
Arg Arg Ile Tyr Asp Leu Ile Glu Leu
  1               5
```

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 25

```
Gln Pro Arg Ala Pro Ile Arg Pro Ile
  1               5
```

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 26

```
Glu Gly Gly Val Gly Trp Arg His Trp
  1               5
```

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 27

```
Cys Leu Gly Gly Leu Leu Thr Met Val
  1               5
```

<210> SEQ ID NO 28
<211> LENGTH: 9
<212> TYPE: PRT
<213> ORGANISM: Artificial Sequence

```
<220> FEATURE:
<223> OTHER INFORMATION: Description of Artificial Sequence:  Synthetic
      Peptide

<400> SEQUENCE: 28

Arg Arg Arg Trp Arg Arg Leu Thr Val
 1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 29

Arg Ala Lys Phe Lys Gln Leu Leu
 1               5

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 30

Arg Lys Cys Cys Arg Ala Lys Phe Lys Gln Leu Leu Gln His Tyr Arg
 1               5                  10                  15

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 31

Gln Val Lys Trp Arg Met Thr Thr Leu
 1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 32

Val Phe Ser Asp Gly Arg Val Ala Cys
 1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 33

Val Pro Ala Pro Ala Gly Pro Ile Val
 1               5
```

```
<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 34

Thr Tyr Ser Ala Gly Ile Val Gln Ile
  1               5

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 35

Leu Leu Asp Phe Val Arg Phe Met Gly Val
  1               5                  10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 36

Gln Asn Gly Ala Leu Ala Ile Asn Thr Phe
  1               5                  10

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 37

Val Ser Ser Asp Gly Arg Val Ala Cys
  1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 38

Val Ser Ser Glu Gly Arg Val Ala Cys
  1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 39

Val Ser Ser Asp Gly Arg Val Pro Cys
  1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 40

Val Ser Ser Asp Gly Leu Val Ala Cys
  1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 41

Val Ser Ser Asp Gly Gln Val Ala Cys
  1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 42

Val Ser Ser Asp Gly Arg Val Val Cys
  1               5

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 43

Val Pro Ala Pro Pro Val Gly Pro Ile Val
  1               5                  10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 44

Val Glu Ile Thr Pro Tyr Glu Pro Thr Gly
  1               5                  10

<210> SEQ ID NO 45
<211> LENGTH: 10
<212> TYPE: PRT
```

```
<213> ORGANISM: Artificial Sequence
<220> FEATURE:
<223> OTHER INFORMATION: Description of Artificial Sequence:  Synthetic
      Peptide

<400> SEQUENCE: 45

Val Glu Ile Thr Pro Tyr Glu Pro Thr Trp
 1               5                  10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 46

Val Glu Leu Thr Pro Tyr Lys Pro Thr Trp
 1               5                  10

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 47

Arg Arg Ile Tyr Asp Leu Ile Lys Leu
 1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 48

Arg Lys Ile Tyr Asp Leu Ile Glu Leu
 1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 49

Pro Tyr Leu Phe Trp Leu Ala Gly Ile
 1               5

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 50

Gln Asn Ala Ala Arg Thr Leu Asn Thr Phe
 1               5                  10
```

EBV CTL EPITOPES

This is a continuation of application Ser. No. 09/194,450, filed Jun. 25, 1999 (now abanonded), which is a U.S. National Application under 35 U.S.C. §371 of International Application No. PCT/AU97/00328 filed on May 23, 1997, which claims priority to AU PO0073 filed on May 24, 1996.

FIELD OF THE INVENTION

The present invention relates to cytotoxic T-cell (CTL) epitopes within Epstein-Barr virus. The present invention also relates to subunit vaccines including CTL epitopes.

BACKGROUND OF THE INVENTION

Epstein-Barr virus (EBV) is a gamma herpesvirus which establishes a latent lifelong infection in the host following acute infection (14,15). While primary infection generally occurs in childhood without significant morbidity, adolescents and young adults may present with the symptoms of acute infectious mononucleosis (IM). The main feature of IM is a self-limiting lymphoproliferation involving both T and B cells accompanied by clinical symptoms such as fever and lymphadenopathy (52,53). Occasionally, the clinical symptoms persist and recur for extended periods after the initial infection. Episodic IM such as this has been described as chronic active EBV infection or, in some cases, severe chronic active EBV infection (35). EBV DNA has been detected in both serum and peripheral blood lymphocytes (PBL) during acute IM with the levels of detectable DNA gradually decreasing as the illness abates (21.22.58).

Evidence for latent EBV infection includes the observation that spontaneous lymphoblastoid cell lines (LCLs), expressing latent proteins, can be regularly established from healthy immune individuals after explantation of either lymph node tissue (34) or fractionated B lymphocytes (59). Although latent EBV infection is usually asymptomatic, sequential studies have established that recrudescence of viral replication in the oral cavity may result in release of infectious virus (59). The exact site of persistence of the virus is uncertain, but the available evidence suggests that small lymphocytes in the circulation harbour the virus in a nonproductive episomal state (24). Accordingly, in asymptomatic donors, EBV DNA is detectable by sensitive PCR analysis in PBL expressing the B-cell marker CD19(29,55).

EBV is also involved in post transplant lymphoproliferative disease, which involves a polyclonal expansion of EBV infected B-cells which is a life threatening lymphoma especially in transplantation patients. EBV is also involved in nasopharyngeal carcinoma and Hodgkinson's disease.

Two types of EBV (types A and B or types 1 and 2) are distinguishable primarily on the basis of variation in the DNA and protein sequences of the latent EBV-associated nuclear antigens (referred to here as EBNAs-2A, -3A, -4A and -6A from the type A virus and EBNAs-2B, -3B, -4B and -6B from the type B virus) (9,46,48). Sequencing of the prototypical isolates of type A and type B EBV (B95-8 and Ag-876 respectively) in these regions revealed 53% amino acid homology between EBNA-2A and EBNA-2B (9) and 72–84% homology between EBNAs-3A and -3B. EBNAs-4A and -4B, and EBNAs-6A and -6B (46). Strain variation due to other DNA alterations or deletions as well as these A/B type differences have been defined at the protein (12) and the DNA level (16,25,26) and recombination between multiple infecting strains was found to occur frequently in oral hairy leukoplakia lesions (56). These variations offer an alternative means of categorising EBV isolates but the primary distinction of type A and type B is still useful. Type A EBV is more readily isolated from healthy donors: type B EBV infections or dual infections with both type A and type B have proven easier to detect in immunosuppressed or HIV infected individuals (5,47,51). A higher incidence of type B infection in some studies led to the suggestion that type B or dual infections are, in fact, relatively common and that resident type B virus levels increase during immunosuppression (3,20,51).

It appears that latent EBV infection is primarily controlled by HLA class I-restricted memory cytotoxic T cell (CTL) responses (reviewed in (18)). These CTL responses can be reactivated in vitro by stimulating lymphocytes from seropositive individuals with autologous lymphoblastoid cell lines (LCLs) which express and present MHC class I and class II restricted epitopes at the cell surface. Several of these epitopes have been identified using target cells infected by recombinant vaccinia constructs (17,19,32,33). Epitopes specific for type A EBV as well as cross-reactive epitopes encoded by both types A and B EBV have been defined (18) but no epitopes specific for type B EBV have been reported thus far. In addition co-pending International Patent Application No. WO 95/001400, the disclosure of which is incorporated herein by cross reference discloses a number of EBV CTL epitopes. In the present study, the response of a donor exposed to both type A and type B EBV was investigated and an epitope specific for type B EBV as well as a new cross-reactive epitope were identified.

SUMMARY OF THE INVENTION

In a first aspect the present invention consists in a cytotoxic Epstein-Barr virus T-cell epitope, the epitope being selected from the group consisting of QVKWRMTTL (SEQ ID NO: 31), VFSDGRVAC (SEQ ID NO: 32), VPAPAGPIV (SEQ ID NO: 33), TYSAGIVQI (SEQ ID NO: 34), LLDFVRFMGV (SEQ ID NO: 35), QNGALAINTF (SEQ ID NO: 36), VSSDGRVAC (SEQ ID NO: 37), VSSEGRVAC (SEQ ID NO: 38), VSSDGRVPC (SEQ ID NO: 39), VSSDGLVAC (SEQ ID NO: 40), VSSDGQVAC (SEQ ID NO: 41), VSSDGRVVC (SEQ ID NO: 42), VPAPPVGPIV (SEQ ID NO: 43), VEITPYEPTG (SEQ ID NO: 44), VEITPYEPTW (SEQ ID NO: 45), VELTPYKPTW (SEQ ID NO: 46), RRIYDLIKL (SEQ ID NO: 47), RKIYDLIEL (SEQ ID NO: 48) and PYLFWLAGI (SEQ ID NO: 49).

In a second aspect the present invention consists in a subunit vaccine, the vaccine including at least one T-cell epitope selected from the group consisting of QVKWRMTTL (SEQ ID NO: 31), VFSDGRVAC (SEQ ID NO: 32), VPAPAGPIV (SEQ ID NO: 33), TYSAGIVQI (SEQ ID NO: 34), LLDFVRFMGV (SEQ ID NO: 35), QNGALAINTF (SEQ ID NO: 36), VSSDGRVAC (SEQ ID NO: 37), VSSEGRVAC (SEQ ID NO: 38), VSSDGRVPC (SEQ ID NO: 39), VSSDGLVAC (SEQ ID NO: 40), VSSDGQVAC (SEQ ID NO: 41), VSSDGRVVC (SEQ ID NO: 42), VPAPPVGPIV (SEQ ID NO: 43), VEITPYEPTG (SEQ ID NO: 44), VEITPYEPTW (SEQ ID NO: 45), VELTPYKPTW (SEQ ID NO: 46), RRIYDLIKL (SEQ ID NO: 47), RKIYDLIEL (SEQ ID NO: 48) and PYLFWLAGI (SEQ ID NO: 49).

In a preferred embodiment of this aspect of the present invention the subunit vaccine includes at least one further epitope selected from the group consisting of TSLYNLRGTALA (SEQ ID NO: 1), DTPLIPLTIF (SEQ ID NO: 2), TVFYNIPPMPL (SEQ ID NO: 3), VEITPYKPTW (SEQ ID NO: 4), VSFIEFVGW (SEQ ID NO: 5), FRKAQIQGL (SEQ ID NO: 6), FLRGRAYGL (SEQ ID NO:7), QAKWR- LQTL (SEQ ID NO: 8), SVRDRLARL (SEQ ID NO: 9), YPLHEQHGM (SEQ ID NO: 10), HLAAQGMAY (SEQ ID NO: 11), RPPIFIRRL (SEQ ID NO: 12), RLRAEAGVK (SEQ ID NO: 13), IVTDFSVIK (SEQ ID NO: 14), AVFDRKSDAK (SEQ ID NO: 15), NPTQAPVIQLVHAVY (SEQ ID NO: 16), LPGPQVTAVLLHEES (SEQ ID NO: 17), DEPASTEPVHDQLL (SEQ ID NO: 18), RYSIFFDY (SEQ ID NO: 19), AVLLHEESM (SEQ ID NO: 20), RRARSLSAERY (SEQ ID NO: 21), EENLLDFVRF (SEQ ID NO: 22), KEHVIQNAF (SEQ ID NO: 23), RRIYDLIEL (SEQ ID NO: 24), QPRAPIRPI (SEQ ID NO: 25), EGGVGWRHW (SEQ ID NO: 26), CLGGLLTMV (SEQ ID NO: 27), RRRWRRLTV (SEQ ID NO: 28), RAKFKQLL (SEQ ID NO: 29) and RKCCRAKFKQLLQHYR (SEQ ID NO: 30).

In a further preferred embodiment of this aspect of the present invention the subunit vaccine includes the cytotoxic T-cell epitopes LLDFVRFMGV (SEQ ID NO: 35), QVKWRMTTL (SEQ ID NO: 31) and FLRGRAYGL (SEQ ID NO:7). An analysis of allele frequency in the HLA listings in the Queensland Institute of Medical Research data base shows that a vaccine including these epitopes would provide protection for 63.7% of the caucasian population.

In a yet further preferred embodiment of this aspect of the present invention the subunit vaccine includes the cytotoxic T-cell epitopes LLDFVRFMGV (SEQ ID NO: 35), QVKWRMTTL (SEQ ID NO: 31), FLRGRAYGL (SEQ ID NO:7) and EENLLDFVRF (SEQ ID NO: 22). An analysis of allele frequency in the HLA listings in the Queensland Institute of Medical Research data base shows that a vaccine including these epitopes would provide protection for 71.1% of the caucasian population.

In another preferred embodiment of this aspect of the present invention the subunit vaccine includes the cytotoxic T-cell epitopes LLDFVRFMGV (SEQ ID NO: 35), QVKWRMTTL (SEQ ID NO: 31), FLRGRAYGL (SEQ ID NO:7) and QPRAPIRPI (SEQ ID NO: 25). An analysis of allele frequency in the HLA listings in the Queensland Institute of Medical Research data base shows that a vaccine including these epitopes would provide protection for 74.1% of the caucasian population.

In a still further preferred embodiment of this aspect of the present invention the subunit vaccine includes the cytotoxic T-cell epitopes LLDFVRFMGV (SEQ ID NO: 35), QVKWRMTTL (SEQ ID NO: 31), FLRGRAYGL (SEQ ID NO:7), EENLLDFVRF (SEQ ID NO: 22) and QPRAPIRPI (SEQ ID NO: 25). An analysis of allele frequency in the HLA listings in the Queensland Institute of Medical Research data base shows that a vaccine including these epitopes would provide protection for 81.5% of the caucasian population. Given the fact that about 50% of all individuals that are not covered by vaccination will become EBV positive without any symptoms, the combination of epitopes listed above will result in a vaccine with more than 90% efficacy. This is of high commercial value.

In a further preferred form of the present invention the vaccine comprises a water-in-oil formulation. It is further preferred that the vaccine includes at least one antigen to which the individual will mount an anamnestic response in addition to the at least one cytotoxic T-cell epitope.

The at least one antigen is preferably selected from the group consisting of tetanus toxoid, diphtheria toxoid, Bordetella pertussis antigens, poliovirus antigens, purified protein derivative (PPD), gp350 protein (Thorley-Lawson, D. A. and Poodry, C. A. (1982). Identification and isolation of the main component (gp350-gp220) of Epstein-Barr virus responsible for generating neutralizing antibodies in vivo. J. Virol. 43, 730–736), helper epitopes and combinations thereof and is preferably tetanus toxoid.

It is preferred that the water-in-oil formulation is Montanide ISA 720. Additional information regarding this formulation can be found in WO 95/24926, the disclosure of which is incorporated herein by cross reference.

The subunit vaccine may also be formulated using ISCOMs. Further information regarding ISCOMs can be found in Australian Patent Nos. 558258, 590904, 632067, 589915, the disclosures of which are included herein by cross reference.

In a third aspect the present invention consists in a nucleic acid vaccine, the vaccine including a nucleic acid sequence encoding at least one of the cytotoxic T-cell epitopes of the first aspect of the present invention and optionally at least one cytotoxic T-cell epitope selected from the group consisting of TSLYNLRRGTALA (SEQ ID NO: 1), DTPLIPLTIF (SEQ ID NO: 2), TVFYNIPPMPL (SEQ ID NO: 3), VEITPYKPTW (SEQ ID NO: 4), VSFIEFVGW (SEQ ID NO: 5), FRKAQIQGL (SEQ ID NO: 6), FLRGRAYGL (SEQ ID NO:7), QAKWRLQTL (SEQ ID NO: 8), SVRDRLARL (SEQ ID NO: 9), YPLHEQHGM (SEQ ID NO: 10), HLAAQGMAY (SEQ ID NO: 11), RPPIFIRRL (SEQ ID NO: 12), RLRAEAGVK (SEQ ID NO: 13), IVTDFSVIK (SEQ ID NO: 14), AVFDRKSDAK (SEQ ID NO: 15), NPTQAPVIQLVHAVY (SEQ ID NO: 16), LPGPQVTAVLLHEES (SEQ ID NO: 17), DEPASTEPVHDQLL (SEQ ID NO: 18), RYSIFFDY (SEQ ID NO: 19), AVLLHEESM (SEQ ID NO: 20), RRARSLSAERY (SEQ ID NO: 21), EENLLDFVRF (SEQ ID NO: 22), KEHVIQNAF (SEQ ID NO: 23), RRIYDLIEL (SEQ ID NO: 24), QPRAPIRPI (SEQ ID NO: 25), EGGVGWRHW (SEQ ID NO: 26), CLGGLLTMV (SEQ ID NO: 27), RRRWRRLTV (SEQ ID NO: 28), RAKFKQLL (SEQ ID NO: 29) and RKCCRAKFKQLLQHYR (SEQ ID NO: 30).

Further information regarding nucleic acid vaccines can be found in WO 96/03144 the disclosure of which is incorporated herein by cross reference. As will be appreciated by those skilled in the field the DNA can be delivered using a suitable viral or bacterial vector.

In a preferred embodiment of this aspect of the present invention the nucleic acid sequence encodes LLDFVRFMGV (SEQ ID NO: 35), QVKWRMTTL (SEQ ID NO: 31) and (FLRGRAYGL (SEQ ID NO:7), or LLDFVRFMGV (SEQ ID NO: 35), QVKWRMTTL (SEQ ID NO: 31), FLRGRAYGL (SEQ ID NO:7) and EENLLDFVRF (SEQ ID NO: 22), or LLDFVRFMGV (SEQ ID NO: 35), QVKWRMTTL (SEQ ID NO: 31), FLRGRAYGL (SEQ ID NO:7) and QPRAPIRPI (SEQ ID NO: 25), or LLDFVRFMGV (SEQ ID NO: 35), QVKWRMTTL (SEQ ID NO: 31), FLRGRAYGL (SEQ ID NO:7), EENLLDFVRF (SEQ ID NO: 22) and QPRAPIRPI (SEQ ID NO: 25).

The vaccines of the present invention may be used prophylactically or therapeutically.

DETAILED DESCRIPTION OF THE INVENTION

The CTL epitopes may be synthesized using techniques well known to those skilled in this field. For example, the CTL epitopes may be synthesised using solution synthesis or solid phase synthesis as described, for example, in Chapter 9 entitled "Peptide Synthesis" by Atherton and Sheppard which is included in a publication entitled "Synthetic Vaccines" edited by Nicholson and published by Blackwell Scientific Publications. Preferably a solid phase support is utilised which may be polystyrene gel beads wherein the polystyrene may be cross-linked with a small proportion of divinylbenzene (e.g. 1%) which is further swollen by lipophilic solvents such as dichloromethane or more polar solvents such as dimethylformamide (DMF). The polystyrene may be functionalised with chloromethyl or anionomethyl groups. Alternatively, cross-linked and functionalised polydimethyl-acrylamide gel is used which may be highly solvated and swollen by DMF and other dipolar aprolic solvents. Other supports can be utilised based on polyethylene glycol which is usually grafted or otherwise attached to the surface of inert polystyrene beads. In a preferred form, use may be made of commercial solid supports or resins which are selected from PAL—PEG, PAK—PEG, KA, KR or TGR.

In solid state synthesis, use is made of reversible blocking groups which have the dual function of masking unwanted reactivity in the a-amino, carboxy or side chain functional groups and of destroying the dipolar character of amino acids and peptides which render them inactive. Such functional groups can be selected from t-butyl esters of the structure RCO—OCMe$_3$—CO—NHR which are known as t-butoxy carboxyl or ROC derivatives. Use may also be made of the corresponding benzyl esters having the structure RCO—OCH$_2$—C$_6$H$_5$ and urethanes having the structure C6H5CH$_2$O CO—NHR which are known as the benzyloxycarbonyl or Z-derivatives. Use may also be made of derivatives of fluorenyl methanol and especially the fluorenylmethoxy carbonyl or Fmoc group. Each of these types of protecting group is capable of independent cleavage in the presence of one other so that frequent use is made, for example, of BOC-benzyl and Fmoc-tertiary butyl protection strategies.

Reference also should be made to a condensing agent to link the amino and carboxy groups of protected amino acids or peptides. This may be done by activating the carboxy group so that it reacts spontaneously with a free primary or secondary amine. Activated esters such as those derived from p-nitrophenol and pentafluorophenyl may be used for this purpose. Their reactivity may be increased by addition of catalysts such as 1-hydroxybenzotriazole. Esters of triazine DHBT (as discussed on page 215–216 of the abovementioned Nicholson reference) also may be used. Other acylating species are formed in situ by treatment of the carboxylic acid (i.e. the Na-protected amino acid or peptide) with a condensing reagent and are reacted immediately with the amino component (the carboxy or C-protected amino acid or peptide). Dicyclohexylcarbodiimide, the BOP reagent (referred to on page 216 of the Nicholson reference), O'Benzotriazole-N,N, N'N'-tetra methyl-uronium hexaflurophosphate (HBTU) and its analogous tetrafluroborate are frequently used condensing agents.

The attachment of the first amino acid to the solid phase support may be carried out using BOC-amino acids in any suitable manner. In one method BOC amino acids are attached to chloromethyl resin by warming the triethyl ammonium salts with the resin. Fmoc-amino acids may be coupled to the p-alkoxybenzyl alcohol resin in similar manner. Alternatively, use may be made of various linkage agents or "handles" to join the first amino acid to the resin. In this regard, p-hydroxymethyl phenylactic acid linked to aminomethyl polystyrene may be used for this purpose.

Details of the CTL epitopes of the present invention are set in Tables 3 and 4.

As will be readily appreciated by those skilled in the art the cytotoxic T-cell epitopes and vaccines of the present invention can be used to protect against EBV. Further given the possible greater involvement of type B EBV infection in immunocompromised individuals the present invention may have particular application in protection of individuals having decreased immune function, eg transplant patients.

In order that the nature of the present invention may be more clearly understood preferred forms thereof will now be described with reference to the following examples and Figures.

MATERIALS AND METHODS

Lymphocyte Donor

Figure 1:
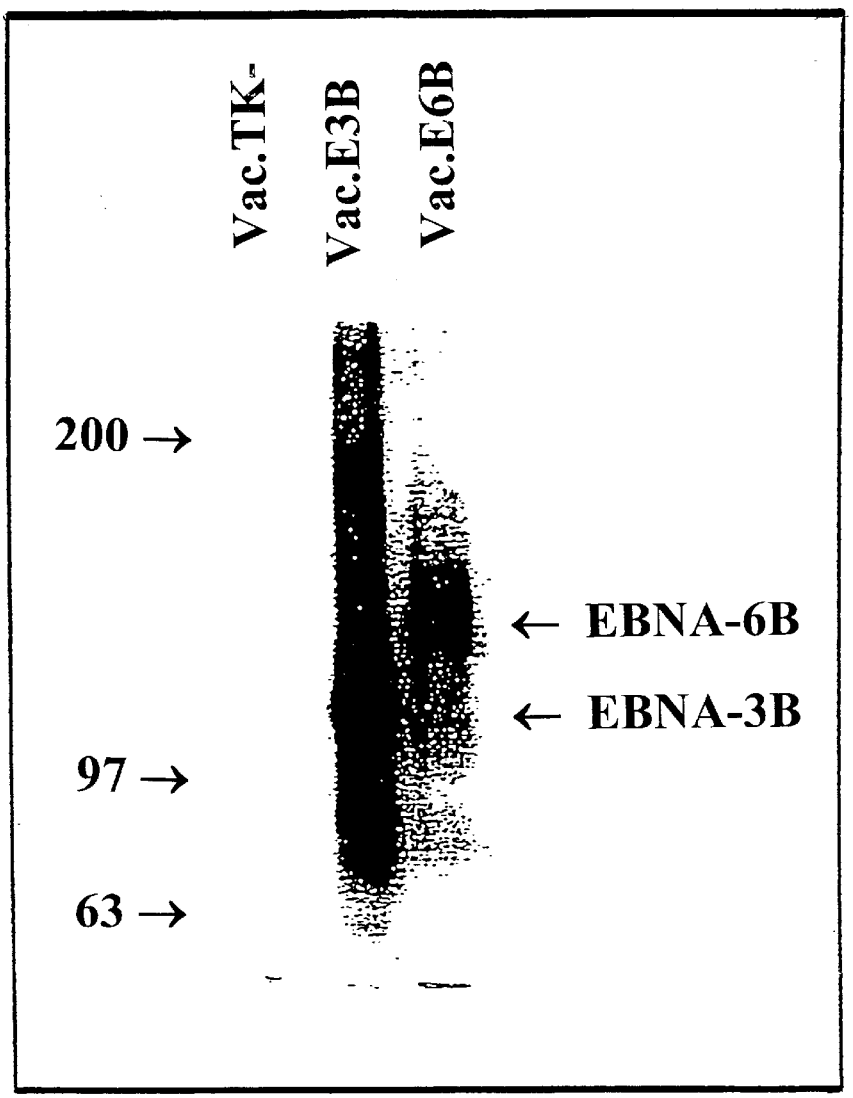
FIG. 1 is a photographic representation of an immunoblot of recombinant vaccinia-5 EBNA virus proteins. The source of recombinant vaccinia viruses is indicated at the top of each lane: Lane 1: vacc-TK-, Lane 2: vacc-EBNA-3B; Lane 3: vacc-EBNA-6B. Molecular weights are indicated at the left of the figure (Da).

A 17 year old individual (EW) who initially presented with clinical and pathological (EBV IgM positive) symptoms of acute IM was used in this study. She was referred to this laboratory for investigation of her EBV status 7 months after the initial diagnosis as her clinical symptoms persisted. Four bleeds were obtained from this donor over a period of 12 months during which time the symptoms fluctuated but did not completely resolve. The third and fourth bleeds were used for CTL analysis.

Virus Typing and Detection

DNA was extracted from PBL by a small scale adaptation of a published extraction procedure (27). EBNA 2A and 2B primers as previously described (20) were used to distinguish between type A and type B EBV by PCR. Briefly, standard PCR reactions were carried out in a 25 $\mu$l volume using 1 $\mu$g genomic DNA. The template was denatured for 2 min at 94° C. before subjecting to 35 PCR cycles (15 s at 94° C. 30 s at 56° C. and 15 s at 72° C.). PCR amplified products were identified on southern blots using digoxigenin-dUTP (DIG) labelled DNA probes (Boehringer-Mannheim Australia) generated by PCR using the same primers as above and either the purified M-ABA Bam HI insert from pM-Bam H2 (type A) (36) or the purified Jijoye Bam HI/Pst I insert from pJ-HKA7 (type B) (1) as templates. For the preparation of the probes, DIG-dUTP was present in the PCR reaction with 25 ng of each insert as template.

Vaccinia Constructs

Recombinant vaccinia constructs (designated vacc-EBNA-1, vacc-EBNA-2 etc) encoding EBNAs-1, -2B, -4A and -6A, the latent membrane proteins LMP1 and LMP2, the lytic antigens BHRF1 and BZLF1, and the control vacc-TK⁻ have already been described (19,23,33). Vacc-EBNA-3B and vacc-EBNA-6B (i.e. vaccinia constructs encoding the type B sequences of EBNA 3 and EBNA 6 respectively) were constructed from an EBV genomic library derived from purified viral genomes of the prototype type B strain Ag-876 (50). The viral DNA was digested with HindIII and ligated into the λ-ZAP cloning system (Integrated Sciences).

An 11.07 kbp HindIIIE fragment encoding the EBNA 3 family open reading frames (ORFs) was subcloned into the vector pUC19. A 2.6 kbp BamHI-CEIII (Klenow-treated) fragment within the region containing the BERF1 ORF of EBNA-3 (46) was isolated and ligated into a BamHI-HindII digest of pBCB07. This vaccinia vector drives recombinant gene expression by the 7.5K vaccinia virus promoter (2). The EBNA-3B sequence encoded in the transfer plasmid was inserted into vaccinia virus by transfection and homologous recombination into the TK gene of vaccinia as described (2). A 4 kbp Eco47III-HindIII fragment within the EBV HindIIIE region containing the BERF2b ORF of EBNA-6B was isolated and ligated into a HindII-HindIII digest of pBCB07. This was subsequently processed as for EBNA-3B.

Integrity of the vacc-EBNA-3B and -6B constructs was confirmed by immunoblot after infection of mouse CV-1 cells. $2 \times 10^5$ CV-1 cells infected with control vaccinia (vacc-TK⁻), vacc-3B or vacc-6B were lysed in protein sample buffer and separated on a 7% SDS-polyacrylamide gel in a Mini-protean II Cell System (Bio-Rad). After transferring to nitro-cellulose the blot was incubated with a multivalent human serum (MCr) which contained EBNA-specific antibodies. The reactions were visualised with the ECL detection system (Amersham). FIG. 1 illustrates the production of a 110 kDa protein (EBNA-3B) or a 130 kDa protein (EBNA-6B) corresponding to the expected products of EBNA-3B and EBNA-6B without the short first ORFs. Sequence analysis also confirmed the integrity of the constructs.

Establishment of Cell Cultures (a) B Cell Cultures: LCLs were established from EW by exogenous transformation of PBL by QIMR-WIL virus (type A; (38)) and Ag-876 (type B). These LCLs were designated EW-WIL and EW AG876. Spontaneous LCLs (i.e. autologous LCLs infected with the donor's endogenous virus strain and designated EW-spon) were established in the presence of cyclosporin (41). LCLs from other donors were transformed by QIMR-WIL. B95-8 or IARC-BL74 virus (30) (type A isolates) or by Ag-876 or QIMR-GOR virus (37) (type B isolates). Other lines used in this study include Burkitt lymphoma cell lines (Chep and Mutu) and the spontaneous line QIMR-WW2-LCL (13,43,44). B cell lines were maintained in RPMI 1640 with 10–20% FCS. (b) T Cell Cultures: Unfractionated PBL were separated on Ficoll-Paque (Pharmacia. Uppsala, Sweden) and stimulated by incubating with γ-irradiated (8000 rads) autologous LCLs (EW-Wil or EW-Ag-876; $2 \times 10^6$ cells per well in 2 ml growth medium without rIL-2, responder:stimulator ratio 50:1) (28). After 3 days the cultures were cloned in agarose (Seaplaque. FMC Corp. Rockland, Me.) and the colonies harvested 3–5 days later. Once established, the T cells were maintained in T cell growth medium (RPMI-1640 supplemented with 15% FCS, 30% MLA-144 supernatant (TIB-201: American type Culture Collection, Rockville, Md. and rIL-2.20 units/ml) (45,57). Since the clonal nature of the T cells was not established, they are referred to in the text as cultures rather than clones. The cultures were routinely maintained in either 24-well plates or tissue culture flasks and restimulated twice weekly with γ-irradiated (8000 rads) autologous LCLs.

Bulk T cell cultures were initially stimulated from the fourth bleed as for cloning but subcultured and maintained after 3–4 days as for T cell colonies. Phytohaemagglutinin (PHA) blasts were generated by stimulation of PBL with PHA (CSL, Melbourne, Australia) and subculturing after 4 days in T cell growth medium. Cultures were regularly screened for mycoplasma contamination.

FACS Analysis

Three-colour cytofluorographic analysis of T cell cultures was performed by means of direct immunofluorescence using labelled monoclonal antibodies specific for CD3

(tricolour-conjugated), CD4 (fluorescein-conjugated), and CD8 (phycoerythrin-conjugated), and (Becton Dickinson, Calif.). The labelled cells were analysed on a FACScan (Becton Dickinson, lysis II software).

Cytotoxicity Assays

T cells were assayed in modified 5-hour $^{51}$Cr-release assays (30). Briefly, target cells were labelled for 1 hour with 0.5–1.0 $\mu$C $^{51}$Cr, washed and resuspended at $10^5$ cells/ml. 50 $\mu$l of target cells were incubated with an equal volume of effectors (Effector:target or E:T ratio generally 10:1) in 96-well V-bottomed microtiter plates, centrifuged, and incubated at 37° C. for 5 hours. After centrifuging again, 25 $\mu$l supernatant was harvested and dried onto 96-well solid scintillation microtiter plates before counting the radioactivity in a Topcount Microplate Scintillation Counter (Packard Instrument Company, Meridan, Conn.).

For determination of antigenic specificity, target cells were infected with vaccinia construct (multiplicity of infection approx. 10:1) and labelled with $^{51}$Cr by a modification of the previously described procedure (17). Both infection and labelling occurred simultaneously for 2.5 hours before washing and using the cells in CTL assays. In some instances target cells were pretreated in V-wells with monoclonal antibodies to HLA-class I (W6/32) or class II (L243) for 30 min at room temperature before adding effector cells.

Regression Assay

The EBV-specific memory CTL response was assessed as previously described (31).

Limiting Dilution Cultures

Limiting dilution cultures were established by distributing PBL from the fourth bleed in 24 replicates at $2\times10^4$ cells per well in 96-well round-bottomed microtitre plates. Doubling dilutions were made to a final concentration of $1.6\times10^2$ per well. Approximately $1\times10^4$ $\gamma$-irradiated (8000 rads) autologous type B (EW-Ag-876) LCLs were added to each well as both feeder and stimulator cells to a total volume of 100 $\mu$l. Cultures were fed on days 4 and 7 with 50 $\mu$l of T cell growth medium and assayed on day 10 or later. The plates were subcultured and maintained in T cell growth medium and stimulated with $\gamma$-irradiated EW-Ag-876 LCLs. Initial assays were against type A and type B LCLs and subsequently against peptide-coated PHA-blasts or LCLs. Precursor frequencies were determined by a modification of the method of maximum likelihood estimation (11). Assessment of peptide specific activity. For determination of the antigenic specificity at the peptide level, a set of 20-mer overlapping peptides of EBNA-6B (residues 100–1069 (46)) was prepared using a kit and software distributed by Chiron Mimotopes (Chiron Corporation, Sydney, Australia). Nine-mer and 10-mer overlapping peptides with unblocked C and N termini were manufactured by Chiron Mimotopes. Labelled target cells were preincubated with overlapping peptides in the 96-well trays for 30–60 minutes before adding effectors. Alternatively, labelled targets were preincubated with a high dose of peptide (40–80 $\mu$g/ml) then washed twice before using in CTL assays. The washing procedure removes the complication of bystander killing in the latter type of experiments (6).

Depletion Experiments

T-cell cultures were depleted of either CD4 or CD8 cells by pretreating with saturating levels of OKT4 (mouse anti-CD4) or OKT8 (mouse anti-CD8) for 30 min on ice before washing twice and incubating with washed Dynabeads M450 (Sheep anti-mouse IgG coated beads, Dynal, A. S. Oslo. Norway) at 4° C. for 60 min with rotation. Beads and adherent cells were removed magnetically and the remaining cells washed once before use in a CTL assay or FACScan analysis.

Results

EBV Typing of Lymphocyte Donor

PCR analysis revealed the presence of both type A and type B EBV in blood from donor EW. The presence of both virus types was supported by the observation that both type A and type B spontaneous cell lines grew out although only the former (referred to as EW-spon) was established in long term culture.

Selection of T-cell Cultures for Analysis

Regression analysis indicated that the donor had memory CTL activity to both virus types. The number of cultures that could be assessed was therefore minimal compared with the T cell responses of most type A donors investigated by this laboratory. Accordingly, 25 colonies from the third sample were assayed and seven of these selected for further study. Three of these cultures (B4, B5 and B7) were type B specific i.e. they lysed autologous type B cells (>15% lysis) but not type A (<10% lysis); the other four (A3, A9, B6, and B9) were A–B specific i.e. they lysed both type A and type B autologous LCLs (>15%) (Table 1).

CTL Analysis of Vaccinia-infected Targets

The seven selected cultures were assayed for CTL activity towards vaccinia-infected autologous type A LCLs (EW-Wil). Four cultures (A3, A9, B4 and B5) gave significant enhancement of CTL activity when vacc-EBNA 6B infected LCLs were compared with control cells or vacc-TK$^-$ infected target cells. Furthermore, these cultures reacted poorly with other EBV sequences (EBNA-1, EBNA-2B, EBNA-3B, EBNA-4A. LMP1, LMP2, BZLF1 and BHRF1) expressed by recombinant vaccinia viruses thus indicating specificity for the vacc-EBNA-6B infected target. Cultures B5 (type B specific) and A3 (crossreactive) were selected for more detailed analysis.

Figure 2A:
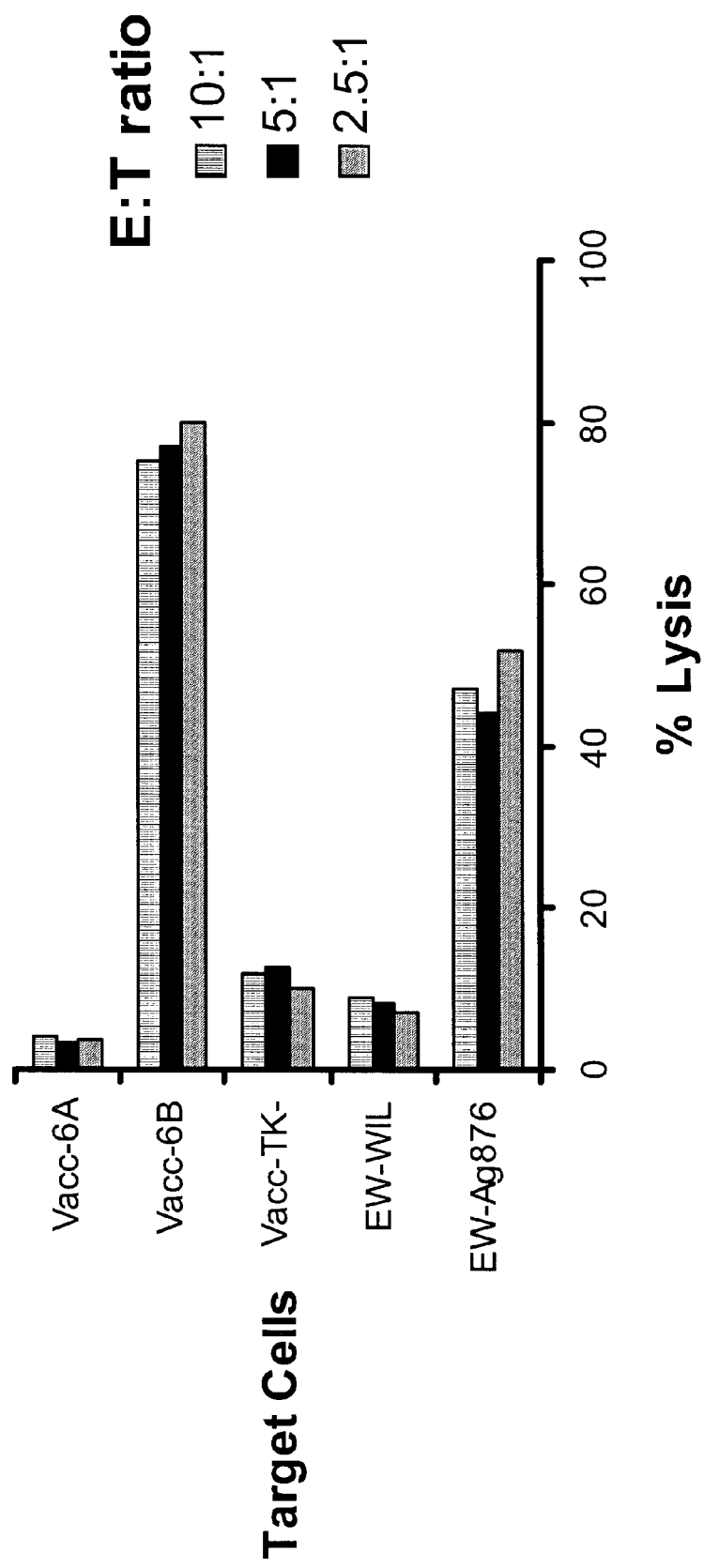
FIG. 2a is a graphical representation showing the percentage lysis of target cells in CTL culture B5. EW-Wil (type A autologous LCL) was infected with the recombinant vaccinia (vacc-EBNA-6A, vacc-EBNA-6B or vacc-TK-), autologous type A LCL (EW-Wil) and autologous type B LCL (EW-Ag-876), as indicated at the left of the figure, and used as targets in a CTL assay. EW-Wil and EW-Ag-876 (type B autologous LCL) were used as control targets without vaccinia infection. Effector-to-target (E:T) ratios in these experiments were as indicated at the right of the figure.
Figure 2B:
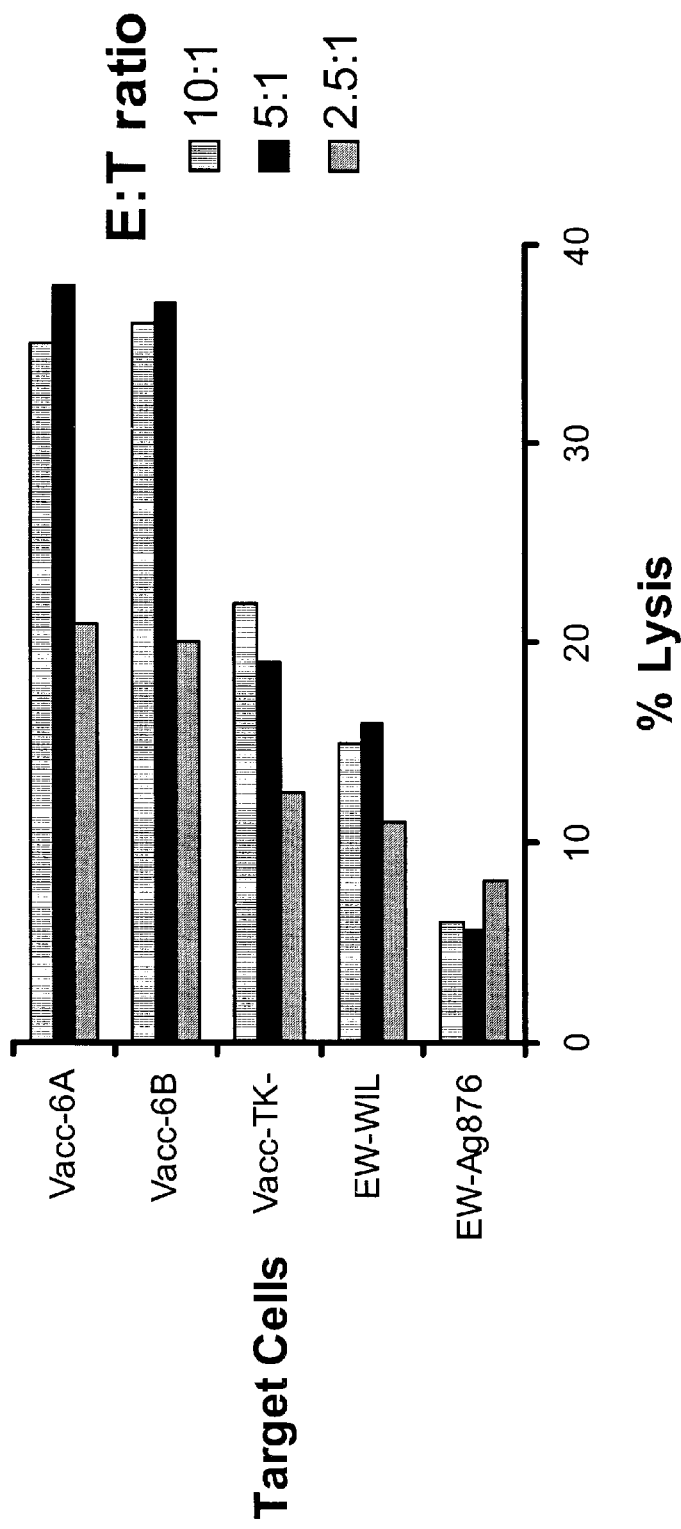
FIG. 2b is a graphical representation showing the percentage lysis of target cells in CTL culture A3. EW-Wil (type A autologous LCL) was infected with the recombinant vaccinia (vacc-EBNA-6A, vacc-EBNA-6B or vacc-TK-), autologous type A LCL (EW-Wil) and autologous type B LCL (EW-Ag-876), as indicated at the left of the figure, and used as targets in a CTL assay. EW-Wil and EW-Ag-876 (type B autologous LCL) were used as control targets without vaccinia infection. Effector-to-target (E:T) ratios in these experiments were as indicated at the right of the figure.

The specificity of cultures A3 and B5 was confirmed in a separate experiment in which EW-Wil target cells were infected with vacc-EBNA-6A and vacc-EBNA-6B. While the CTL activity of colony A3 was enhanced by infection of the target cells with either construct (<10% to 20–37%) the effector function of colony B5 was enhanced only when target cells were infected with vacc-EBNA-6B (<10% to 73–79.5% ) (FIG. 2). These results suggest that culture B5 recognised a type B specific epitope within EBNA-6 while culture A3 recognised a crossreactive epitope within EBNA-6.

Identification of Specific Peptide Targets of CTL Activity

Figure 3A:
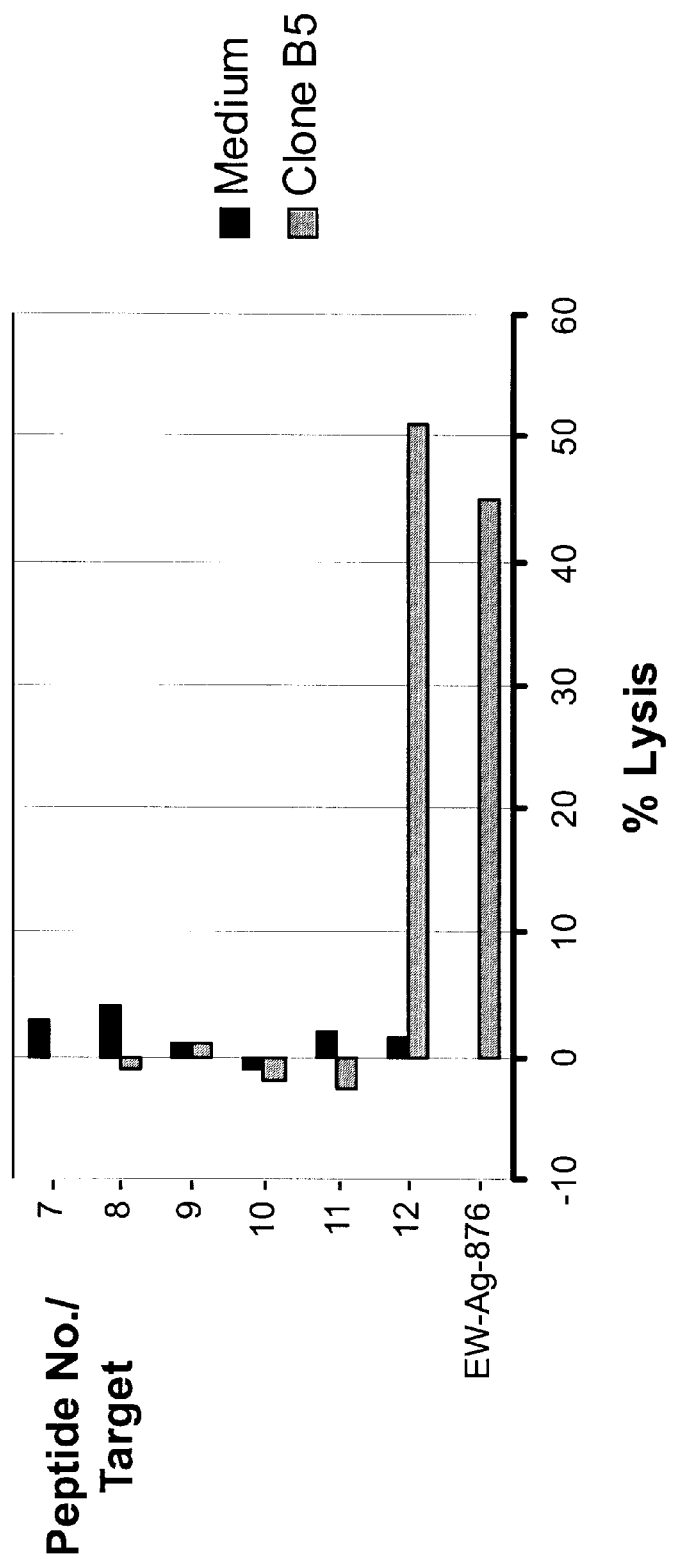
FIG. 3a is a graphical representation showing the percentage lysis of target cells in CTL culture B5 in the presence of medium (filled bars), or overlapping 20-mer epitope peptides numbered 7–12 of EBNA 6B as indicated at the left of the figure (hatched bars). A control target consisting of EW-Ag-876 (type B autologous LCL) without vaccinia infection was also used. Data indicate that the type B specific culture B5 recognised the peptide corresponding to EBNA-6B residues 210–229 (peptide 12 of the EBNA-6B set) when assayed against individual 20-mer overlapping peptides preincubated with autologous PHA blasts.
Figure 3B:
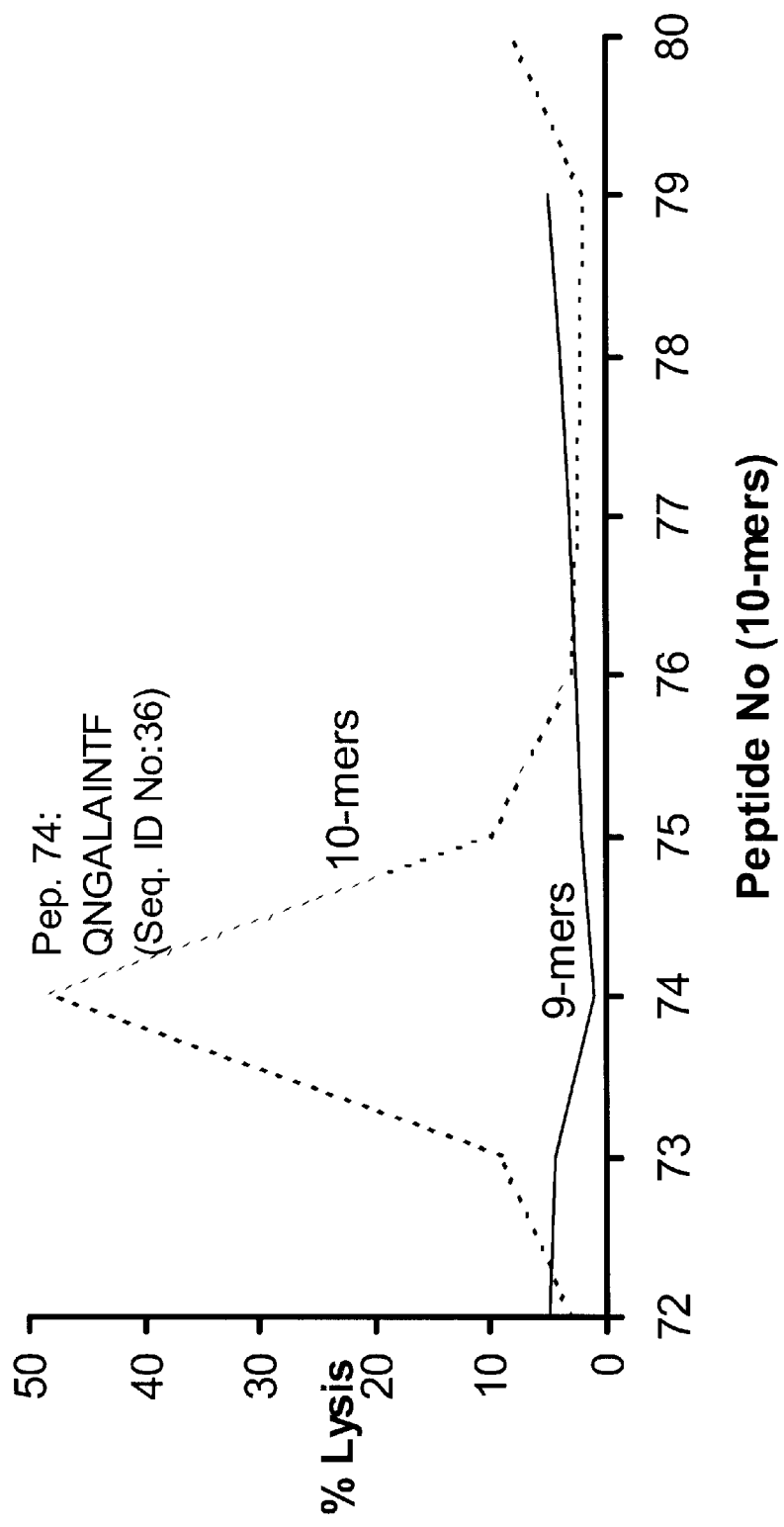
FIG. 3b is a graphical representation showing the percentage lysis of target cells achieved using overlapping 9-mer peptides (unbroken line) or overlapping 10-mer peptides (broken line) derived from the 20-mer peptide No. 12 referred to in the legend to FIG. 3a. Peptide numbers are indicated on the x-axis. Percentage lysis is indicated on the ordinate. Data indicate that the minimal epitope is the 10-mer sequence QNGALAINTF (residues 213–222; SEQ ID NO: 36). The corresponding peptide from the type A overlapping sequence was not recognised by this culture, thus confirming the type B specificity of these T cells.

The type B specific culture B5 recognised the peptide corresponding to EBNA-6B residues 210–229 (peptide 12 of the EBNA-6B set) when assayed against individual 20-mer overlapping peptides preincubated with autologous PHA blasts (FIG. 3a). Nine-mer and 10-mer overlapping peptides were then assayed to identify the minimal 20 epitope as the 10-mer QNGALAINTF (residues 213–222; SEQ ID NO: 36; FIG. 3b). The corresponding peptide from the type A overlapping sequence was not recognised by this culture, thus confirming the type B specificity of these T cells.

Figure 4A:
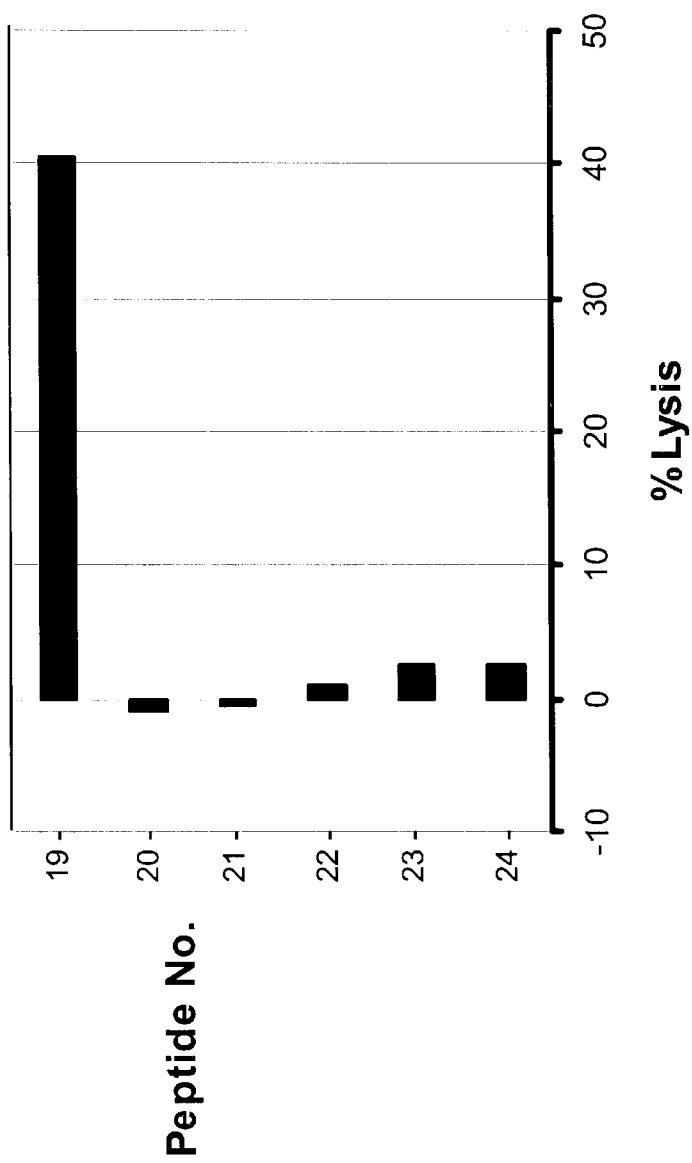
FIG. 4a is a graphical representation showing the percentage lysis of target cells in CTL culture A3 in the presence of overlapping 20-mer epitope peptides numbered 19–24 of EBNA 6B as indicated at the left of the figure (filled bars). Data indicate that the culture A3 recognised peptide 19 of the EBNA-6B set when assayed against individual 20-mer overlapping peptides preincubated with autologous PHA blasts.
Figure 4B:
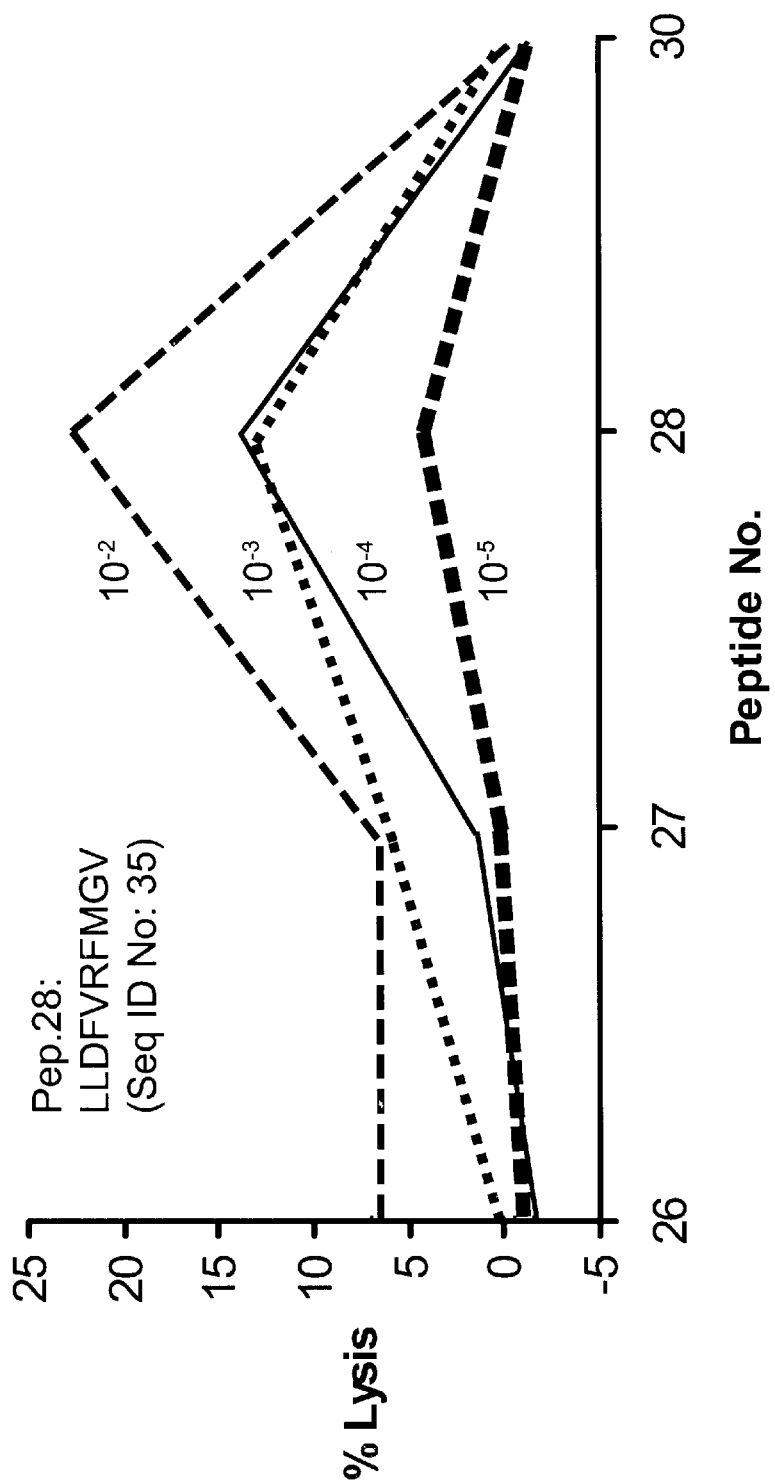
FIG. 4b is a graphical representation showing the percentage lysis of target cells achieved using overlapping 10-mer peptides at various dilutions as indicated of the 20-mer peptide No. 19 (FIG. 4a). Peptide numbers are indicated on the x-axis. Percentage lysis is indicated on the ordinate. Data indicate that the minimal epitope is the 10-mer sequence LLDFVRFMGV (SEQ ID NO: 35) corresponding to residues 284–293 of the EBNA 6A and 6B sequences.

Culture A3 was assayed against pools of overlapping 20-mer peptides from EBNA 6B on autologous PHA-blasts in order to identify its peptide target. A pool containing 6×20-mer peptides (peptides 19–24 in the EBNA-6B set) from residue 280–349 was recognised by this CTL culture and these peptides were subsequently assayed individually to identify the reactive 20-mer as peptide 19, residues 280–299 (FIG. 4a). In FIG. 4b, the minimal epitope was identified as LLDFVRFMGV (SEQ ID NO: 35) corresponding to residues 284–293 of the EBNA 6A and 6B sequences. This sequence is common to both type A and B of EBV and overlaps with the sequence of the B44-restricted epitope EENLLDFVRF (residues 281–290 of EBNA6A and 6B; (7)).

HLA-restriction of Epitopes
(a) Type B Specific Epitope

As Facs assays revealed that cultures recognising the EBNA 6B-encoded sequence QNGALAINTF (SEQ ID NO: 36) contained mixtures of CD4+, CD4+ CD8+ and CD8+ cells when assayed initially, the possibility that the CTL activity was actually due to a CD4 component needed to be eliminated. Several of these cultures also contained components that killed type A autologous targets, presumably because they were derived from the limiting dilution format and contained a mixture of cells. Depletion and inhibition experiments confirmed that the CD8+ cells were the active CTLs.

Figure 5:
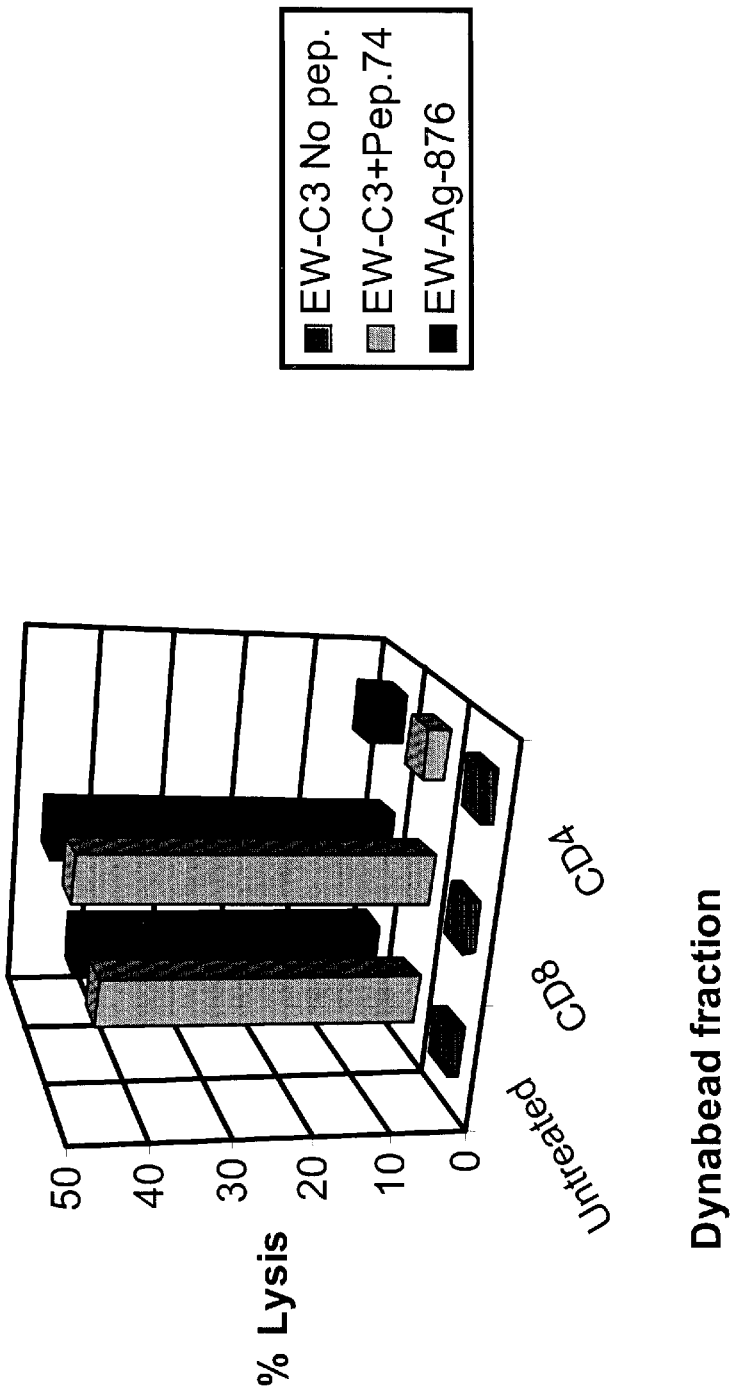
FIG. 5 is a graphical representation showing that depletion of CD8+ cells, but not depletion of CD4+ cells, abrogates epitope specific activity induced by the 20-mer peptide 74. Targets: EW-C3 (negative T cell culture); Effectors: EW type B epitope specific cultures pooled from LDA cultures. EW=CTL treated with Dynabeads only; EW-CD-8: CTL depleted of CD4 T cells; EW-CD4: CTL depleted of CD8 T cells.
Figure 6:
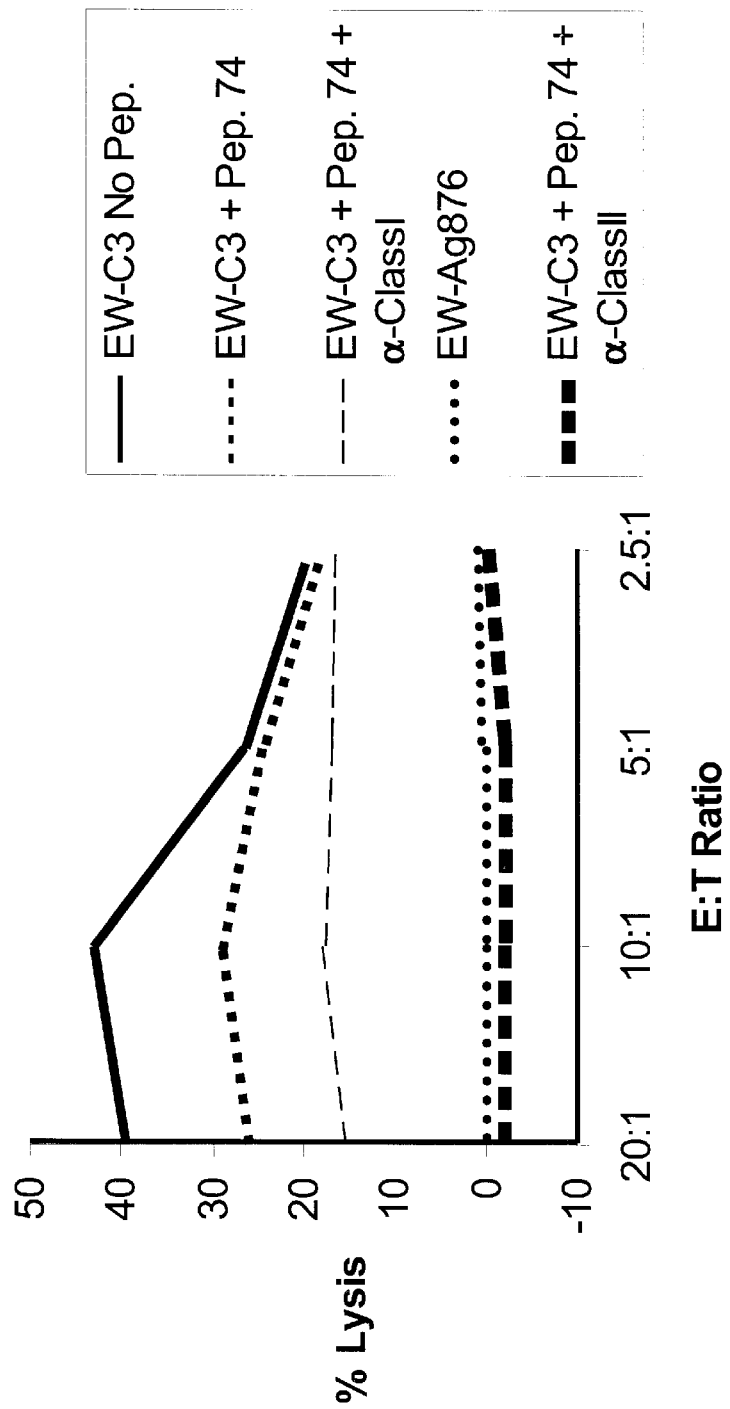
FIG. 6 is a graphical representation showing inhibition of type B epitope-positive CTL (culture B-15) by a-Class I but not by a-Class II monoclonal antisera. Peptide 74 is a type B reactive peptide; target cells were EW-C3, a noncytolytic T cell culture

In the depletion experiments, Dynabeads were used to deplete either CD4+ or CD8+ cells from reactive cultures. When samples of three different epitope-reactive cultures were tested, depletion of the CD4+ cells (which would have included the CD4+ CD8+ component) did not reduce the CTL activity, but depletion of the CD8+ cells completely abrogated the epitope specific activity (FIG. 5). Facs analysis in one of these experiments confirmed that the active fraction contained the CD8+ cells and that both the CD4+ and the CD4+-CD8+ cells had been removed. FIG. 6 illustrates the inhibition of the specific CTL activity of the mixed cultures by anti-class I monoclonal antiserum but not by the anti-class II serum that was positive for DR, DP and DQ alleles. It was concluded therefore that this epitope was Class I-restricted.

In order to identify the restricting allele, LCLs, Burkitt's lymphoma cell lines or PHA blasts of known HLA specificity were incubated with minimalised peptides and washed before using as target cells in CTL assays. As Table 2 indicates, the only target cells killed by the QNGALAINTF (SEQ ID NO: 36) specific CTLs were those that were both A201 and B62 (B15) positive. In contrast, targets that were A201 but not B62, and target cells that only shared A24 or B51 alleles with the donor were not killed. It was therefore concluded that the epitope is B62 (B15)-restricted. B62 which comprises at least 5 subtypes has recently been reclassified as part of the B15 family.

(b) Cross-reactive Epitope

In similar experiments, culture A3 consistently recognised cells bearing HLAA201 but not cells bearing A24, B51, or B62. Furthermore, the CTL activity of this culture was inhibited by anti-class I antibodies but not by anti-class II antibodies. Finally, the A3 minimal epitope corresponds to the motif already identified for HLAA201 restriction (39). It was therefore concluded that the epitope LLDFVRFMGV (SEQ ID NO: 35) corresponding to residues 284–293 in both EBNA-6A and EBNA-6B was HLA Class I A201 restricted.

Predominance of Type B CTL Response in Limiting Dilution Cultures and Bulk Cultures Limiting dilution culture methodology was used in order to investigate the magnitude of the type B specific CTL response. PBL stimulated by a feeder layer of irradiated autologous type B cells were assayed after 10 days against type A and type B autologous LCLs. The results indicated a higher frequency of T cell precursors killing type B LCLs than of those killing type A LCLs. There were therefore a number of wells at limiting dilutions that were type B specific. In general, the wells manifesting type B specific activity retained this specificity. After minimalising the epitopes as described above, the cultures were retested for epitope specific activity. A frequency of 1/16395 was calculated for the Type B epitope QNGALAINTF (SEQ ID NO: 36) compared with 1/304,890 for the A-B specific epitope LLDFVRFMGV (SEQ ID NO: 35) when these cultures were assayed 12 weeks later.

Additional EBV CTL epitopes where obtained from other donors using similar methods.

DISCUSSION

The identification of an EBV type B specific epitope represents the first demonstration of a CTL epitope encoded within type B specific regions of the EBV genome. The epitope was identified as QNGALAINTF (SEQ ID NO: 36) corresponding to residues 213–222 of EBNA-6B. The collective data presented here indicates that stimulation of T cells from donor EW by autologous type B infected LCLs reactivated a predominantly type B response rather than a cross-reactive response. The specificity of the type B response could be maintained on extended culture in vitro. Clearly the response to QNGALAINTF (SEQ ID NO: 36) would seem to be an immunodominant one as indicated by the number of reactive wells in the limiting dilution cultures. It is also interesting to note that a number of type B- specific CTL cultures were established for which specific epitopes could not be identified. It is possible that the target epitopes for these T cells lie within EBNA-4B or outside the regions included in the EBNA-2B, -3B and -6B constructs.

The epitope QNGALAINTF (SEQ ID NO: 36) appears to be restricted through HLA B62 (B15), although the subtype specificity has yet to be determined. Motifs for B*1501 have previously been published (39) and F is commonly found in the last anchor position (9 or 10) as in the epitope identified here. Q or L appear to be the preferred residues at position 2 of B*1501; for the new epitope, Q is at position 1. The corresponding type A sequence for this peptide (QNAARTLNTF) (SEQ ID NO: 50) was nonreactive in CTL assays, thus confirming the type B specificity of the epitope.

A second epitope LLDFVRFMGV (SEQ ID NO: 35) also represents a previously unrecognised EBV-encoded epitope. This sequence corresponds to residues 284–293 of both EBNA-6A and 6B and was shown to be restricted by HLAA201.

An interesting facet of this work was the detection of both type A and type B EBV in the one donor by PCR of both PBL and spontaneous cell lines. Although the available evidence indicates a high prevalence of type B in the community, it is known that in healthy donors type A predominates as the one that is easiest to isolate. Until now, responses to type A virus have therefore been easier to identify.

It was noted in the results section that the donor did not give a particularly active cloning response. It is possible that the type B viruses are less immunogenic than type A, or even that type B EBV has evolved in part to evade the immune system. Type B viruses could conceivably normally be resident in the epithelial compartment rather than the lymphocyte compartment due to their lower transformation efficiency. In this situation, type B epitopes may not be readily presented to the immune system. As already implied, the lower transformation efficiency of type B viruses (42) may hinder reinforcement over time of the immune response to the latency antigens.

Finally, it is important when considering the possibility of vaccinating against EBV to recognise that it may be necessary to vaccinate against both type A and type B. If a patient, particularly a transplant patient at risk of EBV-related post-transplant lymphoma (8), is protected against type A but not type B, there may even be greater risk of clinical disease if subsequently infected with the other virus type. It is particularly important to consider EBV type B epitopes in view of the finding that type B is commonly detected in immunosuppressed individuals. Subunit vaccines against EBV are currently being trialed. In the long term, such vaccines would ideally contain cross-protective specificities. Definition of type B and cross-reactive epitopes allows development of a more effective vaccine, more effective in terms of the range of EBV specificities and HLA types that are covered by the vaccine.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Bibliography

1. Adldinger, H. K., H. Delius, U. K. Freese, J. Clarke, and G. W. Bornkamm. 1985. A putative transforming gene of Jijoye virus differs from that of Epstein-Barr virus prototypes. Virology 141:221–234.
2. Andrew, M. E., B. E. Coupar, D. B. Boyle, and G. L. Ada. 1987. The roles of influenza virus haemagglutinin and nucleoprotein in protection: analysis using vaccinia virus recombinants. Scand. J. Immunol. 25:21–28.
3. Apolloni, A. and T. B. Sculley. 1994. Detection of A-type and B-type Epstein-Barr virus in throat washings and lymphocytes. Virology 202:978–981.
4. Bogedain, C., H. Wolf, S. Modrow, G. Stuber. and W. Jilg. 1995. Specific cytotoxic T lymphocytes recognize the immediate-early transactivator Zta of Epstein-Barr virus. J. Virol. 69:4872–4879.
5. Buisson, M., P. Morand, O. Genoulaz, M. J. Bourgeat, M. Micoud, and J. M. Seigneurin. 1994. Changes in the dominant Epstein-Barr virus type during human immunodeficiency virus infection. J. Gen. Virol. 75:431–437.
6. Burrows, S. R., A. Fernan, V. Argaet, and A. Suhrbier. 1993. Bystander apoptosis induced by CD8+ cytotoxic T cell (CTL) clones: implications for CTL lytic mechanisms. Int. Immunol. 5:1049–1058.
7. Burrows, S. R., I. S. Misko, T. B. Sculley, C. Schmidt, and D. J. Moss. 1990. An Epstein-Barr virus-specific cytotoxic T-cell epitope present on A- and b-type transformants. J. Virol. 64:3974–3976.
8. Crawford, D. H., J. A. Thomas, G. Janossy, P. Sweny, O. N. Fernando. J. F. Moorhead, and J. H. Thompson. 1980. Epstein Barr virus nuclear antigen positive lymphoma after cyclosporin A treatment in patient with renal allograft. Lancet 1:1355–1356.
9. Dambaugh, T., K. Hennessy, L. Chamnankit, and E. Kieff. 1984. U2 region of Epstein-Barr virus DNA may encode Epstein-Barr nuclear antigen 2. Proc. Natl. Acad. Sci. U. S A. 81:7632–7636.
10. Doherty, P. C., R. A. Tripp, and J. W. Sixbey. 1994. Evasion of host immune responses by tumours and viruses. Ciba. Found. Symp. 187:245–256.
11. Fazekas de St Groth, S. 1982. The evaluation of limiting dilution assays. J. Immunol. Methods 49:R11–23.
12. Gratama, J. W., M. A. Oosterveer, W. Weimar, K. Sintnicolaas, W. Sizoo, R. L. Bolhuis, and I. Ernberg. 1994. Detection of multiple 'Ebnotypes' in individual Epstein-Barr virus carriers following lymphocyte transformation by virus derived from peripheral blood and oropharynx. J. Gen. Virol. 75:85–94.
13. Gregory, C. D., M. Rowe. and A. B. Rickinson. 1990. Different Epstein-Barr virus-B cell interactions in phenotypically distinct clones of a Burkitt's lymphoma cell line. J. Gen. Virol. 71:1481–1495.
14. Henle. G., E. T. Lennette, M. A. Alspaugh. and W. Henle. 1979. Rheumatoid factor as a cause of positive reactions in tests for epstein-barr virus-specific IgM antibodies. Clin. Exp. Immunol. 36:415–422.
15. Henle, W. and G. Henle. 1979. Seroepidemiology of the Virus, p. 61–78. In M. A. Epstein and B. G. Achong (eds.), The Epstein-Barr Virus. Springer-Verlag, Berlin.
16. Hu, L. F., J. Minarovits, S. L. Cao, B. Contreras-Salazar, L. Rymo, K. Falk, G. Klein, and I. Ernberg. 1991. Variable expression of latent membrane protein in nasopharyngeal carcinoma can be related to methylation status of the Epstein-Barr virus BNLF-15'-flanking region. J. Virol. 65:1558–1567.
17. Khanna, R., S. R. Burrows, M. G. Kurilla, C. A. Jacob, I. S. Misko, T. B. Sculley, E. Kieff, and D. J. Moss. 1992. Localization of Epstein-Barr virus cytotoxic T-cell epitopes using recombinant vaccinia: implications for vaccine development. J. Exp. Med. 176:169–176.
18. Khanna, R., S. R. Burrows, and D. J. Moss. 1995. Immune regulation in Epstein-Barr virus-associated diseases. Microbiol. Rev. 59:387–405.
19. Khanna, R., C. A. Jacob, S. R. Burrows, M. G. Kurilla, E. Kieff, I. S. Misko, and D. J. Moss. 1991. Expression of Epstein-Barr virus nuclear antigens in anti-IgM-stimulated B cells following recombinant vaccinia infection and their recognition by human cytotoxic T-cells. Immunology 74:504–510.
20. Kyaw, M. T., L. Hurren, L. Evans, D. J. Moss, D. A. Cooper, E. Benson, D. Esmore, and T. B. Sculley. 1992. Expression of B-type Epstein-Barr virus in HIV-infected patients and cardiac transplant recipients. AIDS Res. Hum. Retroviruses 8:1869–1874.
21. Landau, Z., R. Gross, A. Sanilevich, A. Friedmann, and S. Mitrani Rosenbaum. 1994. Presence of infective Epstein-Barr virus in the urine of patients with infectious mononucleosis. J. Med. Virol. 44:229–233.
22. Laroche, C., E. B. Drouet, P. Brousset, C. Pain, A. Boibieux, F. Biron, J. Icart, G. A. Denoyel, and A. Niveleau. 1995. Measurement by the polymerase chain reaction of the Epstein-Barr virus load in infectious mononucleosis and AIDS-related non-Hodgkin's lymphomas. J. Med. Virol. 46:66–74.
23. Lear, A. L., M. Rowe, M. G. Kurilla, S. Lee, S. Henderson, E. Kieff, and A. B. Rickinson. 1992. The Epstein-Barr virus (EBV) nuclear antigen 1 BamHI F promoter is activated on entry of EBV-transformed B cells into the lytic cycle. J. Virol. 66:7461–7468.
24. Lewin, N., P. Aman, M. G. Masucci, E. Klein, G. Klein, B. Oberg, H. Strander, W. Henle, and G. Henle, 1987. Characterization of EBV-carrying B-cell populations in healthy seropositive individuals with regard to density, release of transforming virus and spontaneous outgrowth. Int. J. Cancer 39:472–476.
25. Lung, M. L., R. S. Chang, M. L. Huang, H. Y. Guo, D. Choy, J. Sham, S. Y. Tsao, P. Cheng, and M. H. Ng. 1990. Epstein-Barr virus genotypes associated with nasopharyngeal carcinoma in southern China. Virology 177:44–53.
26. Miller, C. L., J. H. Lee, E. Kieff, and R. Longnecker. 1994. An integral membrane protein (lmp2) blocks reactivation of epstein-barr virus from latency following surface immunoglobulin crosslinking. Proc. Natl. Acad. Sci. U. S A. 91:772–776.
27. Miller, N. and L. M. Hutt-Fletcher. 1988. A monoclonal antibody to glycoprotein gp85 inhibits fusion but not attachment of Epstein-Barr virus. J. Virol. 62:2366–2372.
28. Misko, L. S., T. D. Soszynski, R. G. Kane, and J. H. Pope. 1984. Factors influencing the human cytotoxic 28. T-cell response to autologous lymphoblastoid cell lines in vitro. Clin. Immunol. Immunopathol. 32:285–297.
29. Miyashita, E. M., B. Yang, K. M. Lam, D. H. Crawford, and D. A. Thorley-Lawson. 1995. A novel form of Epstein-Barr virus latency in normal B cells in vivo. Cell 80:593–601.
30. Moss, D. J., I. S. Misko, S. R. Burrows, K. Burman, R. McCarthy, and T. B. Sculley. 1988. Cytotoxic T-cell clones discriminate between A- and B-type Epstein-Barr virus transformants. Nature 331:719–721.
31. Moss, D. J., A. B. Rickinson, and J. H. Pope. 1978. Long-term T-cell-mediated immunity to Epstein-Barr virus in man. I. Complete regression of virus-induced transformation in cultures of seropositive donor leukocytes. Int. J. Cancer 22:662–668.
32. Murray, R. J., M. G. Kurilla, J. M. Brooks, W. A. Thomas, M. Rowe, E. Kieff, and A. B. Rickinson. 1992. Identification of target antigens for the human cytotoxic T-cell response to Epstein-Barr virus (EBV): implications for the immune control of EBV-positive malignancies. J. Exp. Med. 176:157–168.
33. Murray, R. J., M. G. Kurilla, H. M. Griffin, J. M. Brooks, M. Mackett, J. R. Arrand, M. Rowe, S. R. Burrows, D. J. Moss, E. Kieff, and A. B. Rickinson. 1990. Human cytotoxic T-cell responses against Epstein-Barr virus nuclear antigens demonstrated by using recombinant vaccinia viruses. Proc. Natl. Acad. Sci. U. S A. 87:2906–2910.
34. Nilsson, K., G. Klein, W. Henle, and G. Henle. 1971. The establishment of lymphoblastoid lines from adult and fetal human lymphoid tissue and its dependence on EBV. Int. J. Cancer 8:443–450.
35. Okano, M., S. Matsumoto, T. Osato, Y. Sakiyama, G. M. Thiele, and D. T. Purtilo. 1991. Severe chronic active Epstein-Barr virus infection syndrome. Clin. Microbiol. Rev. 4:129–135.
36. Polack, A., G. Hartl, U. Zimber, U. K. Freese, G. Laux, K. Takaki, B. Hohn, L. Gissmann, and G. W. Bornkamm. 1984. A complete set of overlapping cosmid clones of M-ABA virus derived from nasopharyngeal carcinoma and its similarity to other Epstein-Barr virus isolates. Gene 27:279–288.
37. Pope, J. H., B. G. Achong, M. A. Epstein, and J. Biddulph. 1967. Burkitt lymphoma in New Guinea: establishment of a line of lymphoblasts in vitro and description of their fine structure. J. Natl. Cancer Inst. 39:933–945.
38. Pope, J. H., M. K. Horne, and W. Scott. 1968. Transformation of fetal human leucocytes in vitro by filtrates of a human leukemic cell line containing herpes-like virus. Int. J. Cancer 3:857–844.
39. Rammensee, H. G., T. Friede, and S. Stevanoviic. 1995. MHC ligands and peptide motifs: first listing. Immunogenetics 41:178–228.
40. Ressing, M. E., A. Sette, R. M. Brandt, J. Ruppert, P. A. Wentworth, M. Hartman, C. Oseroff, H. M. Grey, C. J. Melief, and W. M. Kast. 1995. Human CTL epitopes encoded by human papillomavirus type 16 E6 and E7 identified through in vivo and in vitro immunogenicity studies of HLA-A*0201-binding peptides. J. Immunol. 154:5934–5943.
41. Rickinson, A. B., M. Rowe, I. J. Hart, Q. Y. Yao, L. E. Henderson, H. Rabin, and M. A. Epstein. 1984. T-cell-mediated regression of spontaneous and of Epstein-Barr virus-induced B-cell transformation in vitro: studies with cyclosporin A. Cell. Immunol. 87:646–658.
42. Rickinson, A. B., L. S. Young, and M. Rowe. 1987. Influence of the Epstein-Barr virus nuclear antigen EBNA 2 on the growth phenotype of virus-transformed B cells. J. Virol. 61:1310–1317.
43. Rooney, C. M., A. B. Rickinson, D. J. Moss, G. M. Lenoir, and M. A. Epstein. 1984. Paired Epstein-Barr virus-carrying lymphoma and lymphoblastoid cell lines from Burkitt's lymphoma patients: comparative sensitivity to non-specific and to allo-specific cytotoxic responses in vitro. Int. J. Cancer 34:339–348.
44. Rooney, C. M., M. Rowe, L. E. Wallace, and A. B. Rickinson. 1985. Epstein-Barr virus-positive Burkitt's lymphoma cells not recognized by virus-specific T-cell surveillance. Nature 317:629–631.
45. Rosenberg, S. A., E. A. Grimm, M. McGrogan, M. Doyle, E. Kawasaki, K. Koths, and D. F. Mark. 1984. Biological activity of recombinant human interleukin-2 produced in *Escherichia coli*. Science 223:1412–1414.
46. Sample, J. and E. Kieff. 1990. Transcription of the Epstein-Barr virus genome during latency in growth-transformed lymphocytes. J. Virol. 64:1667–1674.
47. Sculley, T. B., A. Apolloni, L. Hurren, D. J. Moss, and D. A. Cooper. 1990. Coinfection with A- and B-type Epstein-Barr virus in human immunodeficiency virus-positive subjects. J. Infect. Dis. 162:643–648.
48. Sculley, T. B., A. Apolloni, R. Stumm, D. J. Moss, N. Mueller-Lantzsch, I. S. Misko, and D. A. Cooper. 1989. Expression of Epstein-Barr virus nuclear antigens 3, 4, and 6 are altered in cell lines containing B-type virus. Virology 171:401–408.
49. Selin, L. K., S. R. Nahill, and R. M. Welsh. 1994. Cross-reactivities in memory cytotoxic T lymphocyte recognition of heterologous viruses. J. Exp. Med. 179:1933–1943.
50. Silins, S. L., V. P. Argaet, and T. B. Sculley. 1992. Isolation of Epstein-Barr virus genomes using pulse-field gel electrophoresis. Nucleic Acids Res. 20:2901
51. Sixbey, J. W., P. Shirley, P. J. Chesney, D. M. Buntin, and L. Resnick. 1989. Detection of a second widespread strain of Epstein-Barr virus. Lancet 2:761–765.
52. Sumaya, C. V. and Y. Ench. 1985. Epstein-Barr virus infectious mononucleosis in children. I. Clinical and general laboratory findings. Pediatrics 75:1003–1010.
53. Tomkinson, B. E., D. K. Wagner, D. L. Nelson, and J. L. Sullivan. 1987. Activated lymphocytes during acute Epstein-Barr virus infection. J. Immunol. 139:3802–3807.
54. Tussey, L. G., S. Rowland Jones, T. S. Zheng, M. J. Androlewicz, P. Cresswell, J. A. Frelinger, and A. J. McMichael. 1995. Different MHC class I alleles compete for presentation of overlapping viral epitopes. Immunity. 3:65–77.
55. Wagner, H. J., G. Bein, A. Bitsch, and H. Kirchner. 1992. Detection and quantification of latently infected B lymphocytes in Epstein-Barr virus-seropositive, healthy individuals by polymerase chain reaction. J. Clin. Microbiol. 30:2826–2829.
56. Walling, D. M., S. N. Edmiston, J. W. Sixbey, M. Abdel-Hamid, L. Resnick, and N. Raab-Traub. 1992. Coinfection with multiple strains of the Epstein-Barr virus in human immunodeficiency virus-associated hairy leukoplakia. Proc. Natl. Acad. Sci. U. S A. 89:6560–6564.
57. Wang, A., S. D. Lu, and D. F. Mark. 1984. Site-specific mutagenesis of the human interleukin-2 gene: structure-function analysis of the cysteine residues. Science 224:1431–1433.
58. Yamamoto, M., H. Kimura, T. Hironaka, K. Hirai, S. Hasegawa, K. Kuzushima, M. Shibata, and T. Morishima. 1995. Detection and quantification of virus DNA in plasma of patients with Epstein-Barr virus-associated diseases. J. Clin. Microbiol. 33:1765–1768.

59. Yao, Q. Y., A. B. Rickinson, and M. A. Epstein. 1985. A re-examination of the Epstein-Barr virus carrier state in healthy seropositive individuals. Int. J. Cancer 35:35–42.

TABLE 1

Initial Selection of CTL Cultures

| | | Target Cells (% Lysis) | | | Facs Markers (% + ve) | | | |
|---|---|---|---|---|---|---|---|---|
| Culture No. # | EW-Wil (type A) | EW-Ag- 876 (type B) | K562 (NK sensitive) | CD3+ | CD4+ CD3+ | CD8+ CD3+ | CD4+CD8+ CD3+ | Specificity* |
| A3 | 33.8 | 17.0 | 8.2 | 97.5 | 0.3 | 85 | 2 | A-B |
| A9 | 17.7 | 10.0 | 6.1 | 89 | 2 | 82 | 10 | A-B |
| B4 | 6.6 | 16.6 | 4.3 | 93 | 2 | 70 | 0 | B |
| B5 | 5.9 | 23.8 | 7.8 | 95 | 4 | 90.5 | 5.1 | B |
| B6 | 18.5 | 31.3 | 9.6 | 80 | 2 | 66 | 7 | A-B |
| B7 | 8.1 | 30.2 | 4.1 | 86 | 80 | 0 | 1 | B |
| B9 | 16.8 | 7.7 | 4.1 | 87 | 0 | 96 | 0 | A-B |

Cultures designated A were generated by stimulation with type A autologous LCLs; cultures designated B were derived by stimulation with type B autologous LCLs
*A-B specificity: >10% of both type A and B autologous cell lines; type B specificity: <10% lysis of type A and >15% lysis of type B autologous cell lines

TABLE 2

HLA-Restriction of type B-specific and crossreactive epitopes

| TARGET CELLS (Transforming isolate) | EBV TYPE | CLASS I ALLELES | | | | B-type epitope CTL -Pep | B-type epitope CTL +Pep | Cross-reactive epitope CTL -Pep² | Cross-reactive epitope CTL +Pep |
|---|---|---|---|---|---|---|---|---|---|
| EW-PHA BLASTS | — | A2 | A24 | B51 | B62 | − | + | − | ++ |
| RM-LCL (WIL) | A | A101 | A2 | B8 | B62 | − | + | − | ++ |
| LP-LCL (WIL) | A | A2 | A32 | B35 | B62 | − | + | +, − | ++ |
| PGP-LCL (PUY) | A | A1 | A24 | B8 | B14 | − | − | − | − |
| WW II-LCL (WWII) | A | A11 | A24 | B18 | B39 | − | − | − | ((+)) |
| IM-LCL (GOR) | B | A1 | A11 | B51 | B8 | − | NT | − | NT |
| AS-LCL | A, B | A201 | A24 | B51 | B62 | − | NT | NT | NT |
| SB-PHA | — | A201 | A201 | B35 | B57 | − | − | − | + |
| CHEP (BL)¹ | A | A2 | A3 | B7 | | − | − | − | − |
| MUTU (BL) | A | A1 | A2 | B45 | | − | − | − | + |
| TM-LCL (Wil) | A | A11 | A32 | B35 | B15 | − | − | − | − |
| JAP-LCL (Wil) | A | A2 | A28 | B8 | B15 | − | + | − | + |

¹BL = Burkitt's Lymphoma cell lines - used as targets in peptide experiments as the level of background killing is low
²Clone A3 was originally selected on the basis of CTL activity towards both EW-Wil (type A) and EW-Ag-876 (type B) LCL's, but in the above experiments this clone had low activity only towards heterologous Wil-transformed LCL's.
Cultures that recognised either the crossreactive epitope or the type B-specific epitope were tested in CTL assays against heterologous cell lines with or without specific peptide

TABLE 3

| EBV Antigen | Peptide Epitope (SEQ ID NO:) | HLA Restriction | EBV Type |
|---|---|---|---|
| EBNA3A | QVKWRMTTL (SEQ ID NO: 31) | HLA B8 | Type 2 |
| EBNA3A | VFSDGRVAC (SEQ ID NO: 32) | HLA A29 | Type 1 |
| EBNA3A | VPAPAGPIV (SEQ ID NO: 33) | HLA B7 | Type 1 |
| EBNA3B | TYSAGIVQI (SEQ ID NO: 34) | HLA A24 | Type 1 |
| EBNA3C | LLDFVRFMGV (SEQ ID NO: 35) | HLA A2 | Type 1 & 2 |
| EBNA3C | QNGALAINTF (SEQ ID NO: 36) | HLA B62 | Type 2 |
| EBNA3A | VSSDGRVAC (SEQ ID NO: 37) | HLA A29 | Type 1 |
| EBNA3A | VSSEGRVAC (SEQ ID NO: 38) | HLA A29 | Type 1 |
| EBNA3A | VSSDGRVPC (SEQ ID NO: 39) | HLA A29 | Type 1 |
| EBNA3A | VSSDGLVAC (SEQ ID NO: 40) | HLA A29 | Type 1 |
| EBNA3A | VSSDGQVAC (SEQ ID NO: 41) | HLA A29 | Type 1 |
| EBNA3A | VSSDGRVVC (SEQ ID NO: 42) | HLA A29 | Type 1 |
| EBNA3A | VPAPPVGPIV (SEQ ID NO: 43) | HLA B7 | Type 1 |
| EBNA3A | VEITPYEPTG (SEQ ID NO: 44) | HLA B44 | Type 1 |
| EBNA3A | VEITPYEPTW (SEQ ID NO: 45) | HLA B44 | Type 1 |
| EBNA3A | VELTPYKPTW (SEQ ID NO: 46) | HLA B44 | Type 1 |

TABLE 3-continued

| EBV Antigen | Peptide Epitope (SEQ ID NO:) | HLA Restriction | EBV Type |
|---|---|---|---|
| EBNA3C | RRIYDLIKL (SEQ ID NO: 47) | HLA B27 | Type 1 |
| EBNA3C | RIKIYDLIEL (SEQ ID NO: 48) | HLA B27 | Type 1 |
| LMP2A | PYLFWLAGI (SEQ ID NO: 49) | HLA A23 | |

TABLE 4

| EBV Antigen | Peptide Epitope (SEQ ID NO.) | HLA Rest. | EBV Type | Ref. |
|---|---|---|---|---|
| EBNA1 | TSLYNLRRGTALA (SEQ ID NO. 1) | HLA DR1 | Type 1 & 2 | (Khanna 1995A) |
| EBNA2 | DTPLIPLTIF (SEQ ID NO. 2) | HLA B51/A2 | Type 1 | (Schmidt 1991) |
| EBNA2 | TVFYNIPPMPL (SEQ ID NO. 3) | HLA DQ2 | Type 1 | WO 95/24925 |
| EBNA3A | VEITPYKPTW (SEQ ID NO. 4) | HLA B44 | Type 1 | WO 95/24925 |
| EBNA4 | VSFIEFVGW (SEQ ID NO. 5) | HLA B57 | Type 1 | WO 95/24925 |
| EBNA6 | FRKAQIQGL (SEQ ID NO. 6) | HLA B57 | Type 1 | WO 95/24925 |
| EBNA3A | FLRGRAYGL (SEQ ID NO. 7) | HLA B8 | Type 1 | (Burrows 1992) |
| EBNA3A | QAKWRLQTL (SEQ ID NO. 8) | HLA B8 | Type 1 | (Burrows 1994B) |
| EBNA3A | SVRDRLARL (SEQ ID NO. 9) | HLA A2 | Type 1 & 2 | (Burrows 1994B) |
| EBNA3A | YPLHEQHGM (SEQ ID NO. 10) | HLA B35 | Type 1 | (Burrows 1994B) |
| EBNA3A | HLAAQGMAY (SEQ ID NO. 11) | HLA? | Type 1 | (Burrows 1994B) |
| EBNA3A | RPPIFIRRL (SEQ ID NO. 12) | HLA B7 | Type 1 | (Hill 1995) |
| EBNA3A | RLRAEAGVK (SEQ ID NO. 13) | HLA A3 | Type 1 | (Hill 1995) |
| EBNA3B | IVTDFSVIK (SEQ ID NO. 14) | HLA A11 | Type 1 | (Gavioli 1993A) |
| EBNA3B | AVFDRKSDAK (SEQ ID NO. 15) | HLA A11 | Type 1 | (Gavioli 1993A) |
| EBNA3A | *NPTQAPVIQLVHAVY (SEQ ID NO. 16) | HLA A11 | Type 1 | (Gavioli 1993A) |
| EBNA3A | *LPGPQVTAVLLHEES (SEQ ID NO. 17) | HLA A11 | Type 1 | (Gavioli 1993A) |
| EBNA3A | *DEPASTEPVHDQLL (SEQ ID NO. 18) | HLA A11 | Type 1 | (Gavioli 1993A) |
| EBNA3A | RYSIFFDY (SEQ ID NO. 19) | HLA 24 | Type 1 | (Burrows 1992) |
| EBNA3B | AVLLHEESM (SEQ ID NO. 20) | HLA B35 | Type 1 | (Khanna 1995) |
| EBNA3B | RRARSLSAERY (SEQ ID NO. 21) | HLA B27 | Type 1 | (Hill 1995) |
| EBNA3C | EENLLDFVRF (SEQ ID NO. 22) | HLA B44 | Type 1 & 2 | (Burrows 1990) |
| EBNA3C | KEHVIQNAF (SEQ ID NO. 23) | HLA B44 | Type 1 | (Khanna 1992) |
| EBNA3C | RRIYDLIEL (SEQ ID NO. 24) | HLA B27 | Type 1 | (Brooks 1993B) |
| EBNA3C | QPRAPIRPI (SEQ ID NO. 25) | HLA B7 | Type 1 & 2 | (Hill 1995) |
| EBNA3C | EGGVGWRHW (SEQ ID NO. 26) | B44 | | (Morgan 1996) |
| LMP2A | CLGGLLTMV (SEQ ID NO. 27) | HLA A2 | Type 1 & 2 | (Lee 1993B) |
| LMP2A | RRRWRRLTV (SEQ ID NO. 28) | HLA B27 | Type 1 | (Brooks 1993B) |
| Zta | RAKFKQLL (SEQ ID NO. 29) | HLA B8 | | (Bogedain 1995) |
| Zta | *RKCCRAKFKQLLQHYR (SEQ ID NO. 30) | HLA Cw6 | | (Bogedain 1995) |

Bogedain, C., Wolf, H., Modrow, S., Stuber, G., and Jilg, W. (1995). Specific cytotoxic T lymphocytes recognize the immediate-early transactivator Zta of Epstein-Barr virus. J. Virol. 69, 4872–4879.

Brooks, J. M., Murray, R. J., Thomas, W. A., Kurilla, M. G., and Rickinson, A. B. (1993). Different HLA-B27 subtypes present the same immunodominant Epstein-Barr virus peptide. J. Exp. Med. 178, 879–887.

Burrows, S. R., Misko, I. S., Sculley, T. B., Schmidt, C., and Moss, D. J. (1990). An Epstein-Barr virus-specific cytotoxic T-cell epitope present on A- and b-type transformants. J. Virol. 64, 3974–3976.

Burrows, S. R., Rodda, S. J., Suhrbier, A., Geysen, H. M., and Moss, D. J. (1992). The specificity of recognition of a cytotoxic T lymphocyte epitope. Eur. J. Immunol. 22, 191–195.

Burrows, S. R., Gardner, J., Khanna, R., Steward. T., Moss, D. J., Rodda, S., and Suhrbier, A. (1994). Five new cytotoxic T cell epitopes identified within Epstein-Barr virus nuclear antigen 3. J. Gen. Virol. 75, 2489–2493.

Gavioli, R., Kurilla, M. G., de Campos-Lima, P. O., Wallace, L. E., Dolcetti, R., Murray, R. J., Rickinson, A. B., and Masucci, M. G. (1993). Multiple HLA A11-restricted cytotoxic T-lymphocyte epitopes of different immunogenicities in the Epstein-Barr virus-encoded nuclear antigen 4. J. Virol. 67, 1572–1578.

Hill, A., Worth, A., Elliott, T., Rowland-Jones, S., Brooks, J., Rickinson, A., and McMichael, A. (1995). Characterization of two Epstein-Barr virus epitopes restricted by HLA-B7. Eur. J. Immunol. 25, 18–24.

Hill, A. B., Lee, S. P., Haurum, J. S., Murray, N., Yao, Q. Y., Rowe, M., Signoret, N., Rickinson, A. B., and McMichael, A. J. (1995). Class I major histocompatibility complex-restricted cytotoxic T lymphocytes specific for Epstein-Barr virus (EBV)-transformed B lymphoblastoid cell lines against which they were raised. J. Exp. Med. 181, 2221–2228.

Khanna, R., Burrows, S. R., Kurilla, M. G., Jacob, C. A., Misko, I. S., Sculley, T. B., Kieff, E., and Moss, D. J. (1992). Localization of Epstein-Barr virus cytotoxic T-cell epitopes using recombinant vaccinia: implications for vaccine development. J. Exp. Med. 176, 169–176.

Khanna, R., Burrows, S. R., and Moss, D. J. (1995a). Immune regulation in Epstein-Barr virus-associated diseases. Microbiol. Rev. 59, 387–405.

Khanna. R., Burrows, S. R., Steigerwald Mullen, P. M., Thomson, S. A., Kurilla, M. G., and Moss, D. J. (1995b). Isolation of cytotoxic T lymphocytes from healthy seropositive individuals specific for peptide epitopes from Epstein-Barr virus nuclear antigen 1: implications for viral persistence and tumor surveillance. Virology 214, 633–637.

Lee, S. P., Thomas, W. A., Murray, R. J., Khanim, F., Kaur, S., Young, L. S., Rowe, M., Kurilla, M., and Rickinson, A. B. (1993). HLA A2.1-restricted cytotoxic T-cells recognizing a range of Epstein-Barr virus isolates through a defined epitope in latent membrane. J. Virol. 67, 7428–7435.

Morgan, S. M., Wilkinson, G. W., Floettmann, E., Blake, N., and Rickinson, A. B. (1996). A recombinant adenovirus expressing an Epstein-Barr virus (EBV) target antigen can selectively reactivate rare components of EBV cytotoxic T-lymphocyte memory in vitro. J Virol 70, 2394–2402.

Schmidt, C., Burrows, S. R., Sculley, T. B., Moss, D. J., and Misko, I. S. (1991). Nonresponsiveness to an immunodominant Epstein-Barr virus-encoded cytotoxic T-lymphocyte epitope in nuclear antigen 3a: implications for vaccine strategies. Proc. Natl. Acad. Sci. U. S A. 88, 9478–9482.

What is claimed is:

1. An isolated peptide consisting essentially of a T-cell epitope having the amino acid sequence TYSAGIVQI (SEQ ID NO: 34).

2. An isolated peptide consisting of a T-cell epitope having the amino acid sequence TYSAGIVQI (SEQ ID NO: 34).

3. A composition comprising a peptide consisting essentially of a T-cell epitope having the amino acid sequence TYSAGIVQI (SEQ ID NO:34) in combination with an adjuvant.

4. The composition of claim 3 wherein the adjuvant is montanide ISA 720.

5. The composition of claim 3 wherein the adjuvant comprises Quillaia saponins, cholesterol and phospholipids.

6. A composition comprising a peptide consisting of a T-cell epitope having the amino acid sequence TYSAGIVPI (SEQ ID NO:34) and an adjuvant.

7. The composition of claim 6 wherein the adjuvant is montanide ISA 720.

8. The composition of claim 6 wherein the adjuvant comprises Quillaia saponins, cholesterol and phospholipids.

9. The composition of claim 3 wherein said composition is a water-in-oil emulsion.

10. The composition of claim 6 wherein said composition is a water-in-oil emulsion.

* * * * *

UNITED STATES PATENT AND TRADEMARK OFFICE
CERTIFICATE OF CORRECTION

PATENT NO. : 6,699,477 B2
DATED : March 2, 2004
INVENTOR(S) : Rajiv Khanna et al.

It is certified that error appears in the above-identified patent and that said Letters Patent is hereby corrected as shown below:

Title page,
Item [75], Inventors, please delete "Herston" and insert -- Queensland -- therefor; please delete "Gumdale" and insert -- Queensland -- therefor; please delete "St. Lucia" and insert -- Queensland -- therefor; please delete "Arana Hills" and insert -- Queensland -- therefor; please delete "Bald Hills" and insert -- Queensland -- therefor.
Item [73], Assignee, please delete "Wells" and insert -- Wales -- therefor.

Column 40,
Line 2, please delete "TYSAGIVPI" and insert -- TYSAGIVQI -- therefor.

Signed and Sealed this

Tenth Day of August, 2004

JON W. DUDAS
*Acting Director of the United States Patent and Trademark Office*